United States Patent
Pudil et al.

(10) Patent No.: US 10,905,816 B2
(45) Date of Patent: Feb. 2, 2021

(54) SODIUM MANAGEMENT SYSTEM FOR HEMODIALYSIS

(71) Applicant: Medtronic, Inc., Minneapolis, MN (US)

(72) Inventors: Bryant J. Pudil, Plymouth, MN (US); Martin T. Gerber, Maple Grove, MN (US); David B. Lura, Maple Grove, MN (US); Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 502 days.

(21) Appl. No.: 13/757,794

(22) Filed: Feb. 2, 2013

(65) Prior Publication Data
US 2014/0158623 A1 Jun. 12, 2014

Related U.S. Application Data

(60) Provisional application No. 61/735,348, filed on Dec. 10, 2012.

(51) Int. Cl.
*A61M 1/28* (2006.01)
*A61M 1/16* (2006.01)
*A61M 1/34* (2006.01)

(52) U.S. Cl.
CPC .......... *A61M 1/287* (2013.01); *A61M 1/1656* (2013.01); *A61M 1/1666* (2014.02); *A61M 1/1668* (2014.02); *A61M 1/1696* (2013.01); *A61M 1/3406* (2014.02); *A61M 1/3472* (2013.01); *A61M 1/3479* (2014.02); *A61M 1/3486* (2014.02)

(58) Field of Classification Search
None
See application file for complete search history.

(56) References Cited

U.S. PATENT DOCUMENTS

| | | | |
|---|---|---|---|
| 3,506,126 A | 4/1970 | Lindsay, Jr. | |
| 3,608,729 A | 9/1971 | Haselden | |
| 3,669,878 A | 6/1972 | Marantz | |
| 3,669,880 A | 6/1972 | Marantz | |
| 3,692,648 A | 9/1972 | Matloff | |
| 3,850,835 A | 11/1974 | Marantz | |
| 3,884,808 A | 5/1975 | Scott | |

(Continued)

FOREIGN PATENT DOCUMENTS

| | | |
|---|---|---|
| CN | 101883594 A | 11/2010 |
| CN | 103889481 A1 | 6/2014 |

(Continued)

OTHER PUBLICATIONS

U.S. Appl. No. 13/757,794, filed Feb. 2, 2013.

(Continued)

*Primary Examiner* — Jonathan M Peo

(57) ABSTRACT

Systems and methods for managing the sodium concentration of a dialysate fluid during hemodialysis therapy and adjusting sodium concentration using a sodium management system to generate a sodium-modified fluid are provided. The systems and methods also provide a mechanism for controlled addition of sodium ions to the dialysate to generate a predetermined total sodium concentration in a dialysate.

50 Claims, 17 Drawing Sheets

(56) References Cited

U.S. PATENT DOCUMENTS

| | | |
|---|---|---|
| 3,939,069 A | 2/1976 | Granger |
| 3,989,622 A | 11/1976 | Marantz |
| 4,060,485 A | 11/1977 | Eaton |
| 4,094,775 A | 6/1978 | Mueller |
| 4,136,708 A * | 1/1979 | Cosentino ............ A61M 1/1656 137/99 |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,826,663 A | 4/1989 | Alberti |
| 4,828,693 A | 5/1989 | Lindsay |
| 4,885,001 A | 12/1989 | Leppert |
| 4,900,308 A | 2/1990 | Verkaart |
| 4,977,888 A | 12/1990 | Rietter |
| 5,080,653 A | 1/1992 | Voss |
| 5,092,886 A | 3/1992 | Dobos-Hardy |
| 5,097,122 A | 3/1992 | Coiman |
| 5,114,580 A | 5/1992 | Ahmad |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,419,347 A | 5/1995 | Carruth |
| 5,468,388 A | 11/1995 | Goddard et al. |
| 5,591,344 A | 1/1997 | Kenley |
| 5,662,806 A | 9/1997 | Keshaviah et al. |
| 5,683,432 A | 11/1997 | Goedeke |
| 5,685,835 A | 11/1997 | Brugger |
| 5,702,536 A | 12/1997 | Carruth |
| 5,744,031 A | 4/1998 | Bene |
| 5,762,782 A | 6/1998 | Kenley |
| 5,863,421 A | 1/1999 | Peter |
| 5,944,684 A | 8/1999 | Roberts |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,230,059 B1 | 5/2001 | Duffin |
| 6,248,093 B1 | 6/2001 | Moberg |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | From Herz |
| 6,627,164 B1 | 9/2003 | Wong |
| 6,676,608 B1 | 1/2004 | Keren |
| 6,711,439 B1 | 3/2004 | Bradley |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,878,283 B2 | 4/2005 | Thompson |
| 6,960,179 B2 | 11/2005 | Gura |
| 7,074,332 B2 | 7/2006 | Summerton |
| 7,077,819 B1 | 7/2006 | Goldau |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,318,892 B2 | 1/2008 | Connell |
| 7,500,958 B2 | 3/2009 | Asbrink |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,704,361 B2 * | 4/2010 | Garde .................. B01D 61/445 204/522 |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum et al. |
| 7,785,463 B2 | 8/2010 | Bissler |
| 7,790,103 B2 | 9/2010 | Shah |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum et al. |
| 7,955,291 B2 | 6/2011 | Sternby |
| 7,967,022 B2 | 6/2011 | Grant |
| 7,981,082 B2 | 7/2011 | Wang |
| 8,002,726 B2 | 8/2011 | Karoor |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 1,383,728 A1 | 3/2013 | Pudil |
| 8,409,441 B2 | 4/2013 | Wilt |
| 8,449,448 B2 | 5/2013 | Hovland |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann et al. |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,906,240 B2 | 12/2014 | Crnkovich |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1 | 8/2002 | Wong |
| 2003/0010717 A1 | 1/2003 | Brugger |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 | 1/2004 | Childers |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |

(56) References Cited

U.S. PATENT DOCUMENTS

| | | |
|---|---|---|
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 6/2005 | Childers |
| 2005/0131331 A1 | 6/2005 | Kelly |
| 2005/0131332 A1* | 6/2005 | Kelly ................ A61M 1/1696 604/4.01 |
| 2005/0150832 A1* | 7/2005 | Tsukamoto ......... A61M 1/1696 210/638 |
| 2005/0234381 A1 | 10/2005 | Niemetz |
| 2005/0236330 A1 | 10/2005 | Nier |
| 2005/0274658 A1* | 12/2005 | Rosenbaum ........ A61M 1/1696 210/96.2 |
| 2006/0025661 A1 | 2/2006 | Sweeney |
| 2006/0195064 A1 | 8/2006 | Plahey |
| 2006/0217771 A1 | 9/2006 | Soykan |
| 2006/0226079 A1 | 10/2006 | Mori |
| 2006/0241709 A1 | 10/2006 | Soykan et al. |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0213653 A1 | 9/2007 | Childers |
| 2007/0213665 A1 | 9/2007 | Curtin |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0101549 A1 | 4/2009 | Kamen |
| 2009/0101577 A1 | 4/2009 | Fulkerson |
| 2009/0105629 A1 | 4/2009 | Grant |
| 2009/0124963 A1 | 5/2009 | Hogard |
| 2009/0127193 A1* | 5/2009 | Updyke .............. A61M 1/1696 210/636 |
| 2009/0157877 A1 | 6/2009 | Baek |
| 2009/0159527 A1* | 6/2009 | Mickols .............. B01D 61/025 210/500.38 |
| 2009/0171261 A1 | 7/2009 | Sternby |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0030151 A1 | 2/2010 | Kirsch |
| 2010/0042035 A1 | 2/2010 | Moissl |
| 2010/0078381 A1 | 4/2010 | Merchant |
| 2010/0078387 A1* | 4/2010 | Wong ................. A61M 1/1696 210/656 |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0217180 A1 | 8/2010 | Akonur |
| 2010/0217181 A1 | 8/2010 | Roberts |
| 2010/0224492 A1* | 9/2010 | Ding .................. A61M 1/1696 204/535 |
| 2010/0234795 A1 | 9/2010 | Wallenas |
| 2010/0241045 A1 | 9/2010 | Kelly |
| 2010/0274171 A1 | 10/2010 | Caleffi |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1* | 3/2011 | Ding .................. A61M 1/1696 204/543 |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann et al. |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120946 A1 | 5/2011 | Levin |
| 2011/0130666 A1 | 6/2011 | Dong |
| 2011/0144570 A1 | 6/2011 | Childers |
| 2011/0160637 A1 | 6/2011 | Beiriger |
| 2011/0163030 A1 | 7/2011 | Weaver |
| 2011/0184340 A1 | 7/2011 | Tan |
| 2011/0189048 A1 | 8/2011 | Curtis |
| 2011/0220562 A1 | 9/2011 | Beiriger |
| 2011/0272337 A1 | 11/2011 | Palmer |
| 2011/0284377 A1* | 11/2011 | Rohde ................ A61M 1/1656 204/542 |
| 2011/0315611 A1 | 12/2011 | Fulkerson |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0220926 A1* | 8/2012 | Soykan ................ A61M 1/284 604/28 |
| 2012/0258545 A1 | 10/2012 | Ash |
| 2012/0258546 A1 | 10/2012 | Marran |
| 2012/0259276 A1 | 10/2012 | Childers |
| 2012/0273354 A1* | 11/2012 | Orhan ................. A61M 1/1696 204/519 |
| 2012/0273415 A1 | 11/2012 | Gerber |
| 2012/0273420 A1 | 11/2012 | Gerber |
| 2012/0277546 A1 | 11/2012 | Soykan et al. |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0018301 A1 | 1/2013 | Weaver |
| 2013/0019994 A1 | 1/2013 | Schaer |
| 2013/0030356 A1 | 1/2013 | Ding |
| 2013/0037465 A1 | 2/2013 | Heyes |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky)Britton |
| 2013/0330208 A1 | 12/2013 | Ly |

(56) References Cited

U.S. PATENT DOCUMENTS

| | | |
|---|---|---|
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur et al. |
| 2014/0065950 A1 | 3/2014 | Mendelsohn |
| 2014/0088442 A1 | 3/2014 | Soykan et al. |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0220699 A1 | 8/2014 | Pudil |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |

FOREIGN PATENT DOCUMENTS

| | | |
|---|---|---|
| DE | 3215003 | 4/1985 |
| EP | 266795 A2 | 11/1987 |
| EP | 0743071 | 11/1996 |
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 2740502 | 6/2014 |
| EP | 1787666 | 11/2015 |
| JP | 5099464 | 10/2012 |
| WO | 9937342 | 7/1999 |
| WO | 0057935 | 10/2000 |
| WO | 2000066197 | 11/2000 |
| WO | 2001085295 A2 | 9/2001 |
| WO | 200066197 A1 | 11/2001 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 200170307 A1 | 4/2004 |
| WO | 2004030716 A2 | 4/2004 |
| WO | 2004030717 A2 | 4/2004 |
| WO | 2004064616 A2 | 8/2004 |
| WO | 2004105589 A2 | 12/2004 |
| WO | 2005044339 | 5/2005 |
| WO | 2005061026 | 7/2005 |
| WO | 2005123230 A2 | 12/2005 |
| WO | 2007010164 A2 | 1/2007 |
| WO | 2007089855 A2 | 8/2007 |
| WO | 2007146162 A2 | 12/2007 |
| WO | 20007146162 A3 | 12/2007 |
| WO | 2008037410 | 4/2008 |
| WO | 2009024566 | 2/2009 |
| WO | 2009026603 | 3/2009 |
| WO | 2009026603 A1 | 3/2009 |
| WO | 2009061608 | 5/2009 |
| WO | 2009064984 | 5/2009 |
| WO | 2009071103 | 6/2009 |
| WO | 2009094184 | 7/2009 |
| WO | 2009132839 A1 | 11/2009 |
| WO | 2009157877 | 12/2009 |
| WO | 2009157878 | 12/2009 |
| WO | 0210028860 A1 | 3/2010 |
| WO | 2010028860 A1 | 3/2010 |
| WO | 2010042666 | 4/2010 |
| WO | 2010042666 A2 | 4/2010 |
| WO | 2010096659 | 10/2010 |
| WO | 2010121820 | 10/2010 |
| WO | 2011025705 A1 | 3/2011 |
| WO | 2012026978 | 3/2012 |
| WO | 2012042323 | 4/2012 |
| WO | 2012050781 | 4/2012 |
| WO | 2012051996 | 4/2012 |
| WO | 2012067585 | 5/2012 |
| WO | 12148786 | 11/2012 |
| WO | 12148789 | 11/2012 |
| WO | 2012148781 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013027214 | 2/2013 |
| WO | 2013028809 A3 | 2/2013 |
| WO | 2013019994 A3 | 4/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | 14117000 | 7/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

U.S. Appl. No. 13/757,792, filed Feb. 2, 2013.
U.S. Appl. No. 13/757,722, filed Feb. 1, 2013.
U.S. Appl. No. 13/791,755, filed Mar. 8, 2013.
U.S. Appl. No. 13/837,287, filed Mar. 15, 2013.
PCT Application, PCT/US20013/020404, filed Jan. 4, 2013.
U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
Bleyer, et. al., Sudden and cardiac death rates in hemodialysis patients, Kidney International, 1999, 1553-1559 : 55.
MacLean, et, al., Effects of hindlimb contraction on pressor and muscle interstitial metabolite responses in the cat, J. App. Physiol., 1998, 1583-1592, 85 (4).
Overgaard, et. al., Activity-induced recovery of excitability in K+-depressed rat soieus muscle, Am. J. Physiol. Regulatory integrative Comp. Physiol., 2001, R48-R55, vol. 280.

(56) References Cited

OTHER PUBLICATIONS

Overgaard. et. al., Relations between excitability and contractility in rate soleus'muscle: role of the NA+—K+ pump and NA+—K—S gradients. Journal of Physiology, 1999, 215-225, 518(1).
PCT/US2012/034330, International Search Report, dated Aug. 28, 2012.
PCT/US2012/034332, International Search Report, dated Jul. 5, 2012.
Roberts M, The regenerative dialysis (REDY) sorbent system. Nephrology, 1998, 275-278:4.
Ronco, et. al., "Cardiorenal Syndrome", J. Am. Coll. Cardiol., 2008, 1527-1539 : 52.
Siegenthalar, et. al., Pulmonary fluid status monitoring with intrathoracic impedance, Journal of Clinical Monitoring and Computing, 2010, 449-451 : 24.
U.S. Appl. No. 60/650,497.
U.S. Appl. No. 61/480,535.
U.S. Appl. No. 61/480,539.
U.S. Appl. No. 61/480,541.
U.S. Appl. No. 61/480,544.
Wang, Fundamentals of intrathoracic impedance monitoring in heart failure, Am. J. Cardiology, 2007, 3G-310: Suppl.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, dated Aug. 13, 2013.
PCT/US/2012/034329, International Search Report, dated Dec. 3, 2012.
PCT/US2012/034331, International Search Report, dated Jul. 9, 2012.
PCT/US2012/034334, International Search Report, dated Jul. 6, 2012.
PCT/US2012/034335, International Search Report, dated Sep. 5, 2012.
Redfield, et. al, "Restoration of renal response to atria! natriuretic factor in experimental low-output heat failure", Am. J. Physiol., 1989, R917-923 : 257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Coast, et al. 1990, An approach to Cardiac Arrhythmia analysis Using Hidden Markov Models, IEEE Transactions on Biomedical Engineering. 1990, 37 (9):826-835.
ISA Invitation to Pay Additional Fees, PCT/US2012/034323 mailed Aug. 2, 2012.
U.S. Appl. No. 13/424,429.
U.S. Appl. No. 13/424,479.
U.S. Appl. No. 13/424,525.
U.S. Appl. No. 61/480,528.
U.S. Appl. No. 61/480,530.
U.S. Appl. No. 61/480,532.
Wang, Fundamentals of intrathoracic impedance monitoring in heart failure, Am. J. Cardiology, 2007, 3G-10G : Suppl.

U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
PCT/US2012/034330, International Preliminary Report on Patentability, dated Oct. 29, 2013.
Leifer, I., et al., A Study on the Temperature Variation of Rise Velocity for Large Clean Bubbles, J. Atmospheric & Oceanic Tech., vol. 17, pp. 1392-1402.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, MAR, Terminal Velocity of a Bubble Rise in a Liquid Column, Talaia, World Acad. of Sci., Engineering & Tech., vol. 28, pp. 264-268.
The FHN Trial Group. In-Center. Hemodialysis Six Times per Week versus Three Times per Week, New England Journal of Medicine, 2010.
U.S. Appl. No. 13/757,693, filed Feb. 1, 2013.
PCT/US2014/014357 International Search Report and Written Opinion.
PCT/US2012/034333, International Preliminary Report on Patentability, dated Oct. 29, 2013.
PCT/US2012/034333, International Search Report, dated Aug. 29, 2013.
Welgemoed, T.J., "Capacitive Deionization Technology: An Alternative to desalination Solution," Desalination 183 (2005) 327-340.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
EP13182115.9-1651 European Search Report, dated Feb. 3, 2014.
Written Opinion of the International Searching Authority for PCT/US2012/049398 dated Feb. 25, 2013.
European Search Report 12819714.2-1651/2739325 PCT/US2012049398, dated Jun. 12, 2015.
PCT/US2014/14343 Int'l Search Report & Written Opinion, dated Sep. 2006.
EP 14746791 Supplementary European Search Report dated Aug. 19, 2016.
PCT/US2014/014350 International Search Report and Written Opinion dated May 2014.
EP 14746793 Supplementary European Search Report dated Aug. 18, 2016.
U.S. Appl. No. 29/446,285, filed Feb. 1, 2013.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2014/014345 International Search Report and Written Opinion, dated May 2014.
EP 14746799 Supplementary European Seach Report dated Aug. 18, 2016.
Office Action in U.S. Appl. No. 13/757,792 dated Apr. 6, 2015.
Office Action in U.S. Appl. No. 13/757,792 dated Oct. 27, 2015.
Office Action in U.S. Appl. No. 13/757,792 dated Jun. 2, 2016.
Office Action in U.S. Appl. No. 13/757,792 dated Aug. 26, 2016.
Franks, Gene, Cabon Filtration: What it does, What it doesn't, Mar. 14, 2012, pp. 1-3.
Hamm et al,. "Sorbent regenerative hemodialysis as a potential cuase of acute hypercapnia," Kidney International, vol. 21, (1982), pp. 416-418.
Office Action in Chinese Application No. 201480007132.5 dated Feb. 27, 2017.
Office Action for Chinese Application 201510713880.1 dated Apr. 1, 2017.
Understanding Dialysate Bicarbonate—A simple approach to understanding a complex equation by Fresenius Medical Care, 2011.

(56) References Cited

OTHER PUBLICATIONS

PCT/US2014/014356 International Preliminary Report dated Feb. 26, 2015.
PCT/US2014/014356 International Search Report and Written Opinion dated May 2, 2014.
Office Action in Chinese Application No. 201480007132.5 dated Jun. 28, 2016.
EP 14746222.0 European Search Report dated Oct. 26, 2016.
Office Action for Chinese Application 20148007136.3, dated Jun. 15, 2017.
Office Action in Chinese Application No. 201480007132.5 dated Jul. 19, 2017.
European Office Action in Application 14746793.0 dated Apr. 13, 2017.
Examination report in Australian Application No. 2014212141 dated May 26, 2017.
Indian Office Action for App. No. 2534/KOLNP/2015, dated Sep. 10, 2020.
Examination report for Australian Application No. AU2014212135 dated May 25, 2017.
Office Action in Chinese Application No. 201480007138.2 dated May 31, 2017.

\* cited by examiner

SODIUM MANAGEMENT SYSTEM FOR HEMODIALYSIS

FIELD OF THE INVENTION

The invention relates to systems for managing the sodium concentration of a dialysate fluid during hemodialysis therapy. The present invention provides a mechanism for adjusting sodium concentration using a sodium management system to generate a sodium-modified fluid. The present invention additionally provides a mechanism for controlled addition of sodium ions to the dialysate to generate a predetermined total sodium concentration in a dialysate.

BACKGROUND

During hemodialysis, the dialysate sodium concentration plays an important role in patient outcomes. Performing hemodialysis on a patient with specific dialysate sodium ion concentrations can influence the occurrence of hypotensive episodes, the prevention of disequilibrium syndrome, and the minimization of interdialytic weight gain, among other things. Method and systems to manage sodium dialysate concentration are especially important with systems that contain a component that may change the sodium ion level to unknown values. For example, regenerative hemodialysis systems, such as the Recirculating Dialysate System ("REDY" System), contain sorbent materials that release and/or remove sodium from the dialysate fluid. The removal and/or addition of sodium to the dialysate fluid depend on several factors including: patient blood urea level, patient weight, dialysate composition, sorbent properties, etc. Because of this, it becomes difficult to predict the changes in dialysate sodium concentration that will occur during a hemodialysis session. Expensive sorbet materials can be depleted, and also necessitate complicated management systems to monitor sodium concentration of the dialysate fluid exiting the sorbet system. For example, the "REDY" system requires 6 to 8 liters of water for operation and in some cases the patient is required to remove 1 to 2 liters of dialysate during operation and replace with 1 to 2 liters of fresh water in order to reduce the sodium levels in the dialysate. Therefore, there is a need for systems and methods that can more tightly control the sodium concentration of the dialysate. There is also a need for a system that can control the sodium concentration of the dialysate by removing or adding sodium ions from the working dialysate. There is a need for systems and methods for managing and controlling the sodium that minimize system size and weight and do not require large amounts of fluid or supporting infrastructure.

SUMMARY OF THE INVENTION

The present invention describes a system for kidney replacement therapy and sodium management having a dialysate flow loop for circulating a dialysate through a dialyzer where at least one waste species enters the dialysate and a dialysate regeneration unit for removing at least one waste species. The present invention also provides a mechanism for readjusting the ion concentration in the dialysate by either releasing at least one conductive species to the dialysate or removing at least one conductive species from the dialysate. A detector can measure the conductivity or sodium ion concentration of the dialysate. A sodium management system generates a sodium-modified fluid for controlled addition to the dialysate in the dialysate flow loop wherein the sodium-modified fluid is obtained from any one of an input dialysate, input ultrafiltrate, input solid sodium salt, input concentrated sodium solution, capacitive deionization cell, or electrodialysis cell resulting in a sodium ion concentration or conductivity that is different than the fluid in the original dialysate.

In any embodiment, the system for kidney replacement therapy and sodium management can be controlled compliant. In any embodiment, the system for kidney replacement therapy and sodium management can selectively meter fluid into and out of the dialysate flow loop. In any embodiment, the system for kidney replacement therapy and sodium management can selectively meter fluid into and out of the dialysate flow loop using any one of a control pump, a water pump, a salination pump, an acid concentrate pump, a replacement fluid pump, and combinations thereof. In any embodiment, the system for kidney replacement therapy and sodium management can provide for bi-directional flow.

In any embodiment, a method for modifying the sodium concentration of a dialysate involves circulating a dialysate in a dialysate flow loop wherein the dialysate contacts a dialyzer and a dialysate regeneration unit. The dialysate regeneration unit is contemplated wherein at least one waste species can be partially removed by the dialysate regeneration unit. The method can optionally include operating a control or ultrafiltration pump connected to an ultrafiltrate reservoir for pumping fluid into or out of the dialysate flow loop at a position downstream from the dialyzer and upstream from the dialysate regeneration unit. Operating the control pump in an efflux direction causes a net removal of fluid from the blood on the extracorporeal side of a membrane in the dialyzer to generate an ultrafiltrate added to the ultrafiltrate reservoir. Operation of the control pump in an influx direction causes net addition of fluid to the blood on the extracorporeal side of the membrane. The method can also include modifying the sodium concentration of an input fluid using a sodium management system through application of an electrical field to generate a sodium-modified fluid, the input fluid being dialysate or ultrafiltrate and the input fluid divided into first and second flow streams within the sodium management system; and adding the sodium-modified fluid to the dialysate flow loop.

In any embodiment, the method for modifying the sodium concentration of a dialysate for dialyzing blood can be controlled compliant. In any embodiment, the method for modifying the sodium concentration of a dialysate for dialyzing blood is provided such that the fluid can be selectively metered into and out of the dialysate flow loop. In any embodiment, the method for modifying the sodium concentration of a dialysate for dialyzing blood is provided such that the fluid can be selectively metered into and out of the dialysate flow loop using any one of a control pump, a water pump, a salination pump, an acid concentrate pump, a replacement fluid pump, and combinations thereof. In any embodiment, the method for modifying the sodium concentration of a dialysate for dialyzing blood is provided such that bi-directional flow is provided with the dialysate flow loop.

A control pump or ultrafiltration pump connected to an ultrafiltrate reservoir can be operated for pumping fluid into or out of the dialysate flow loop. The control pump or ultrafiltration pump is located at a position downstream from the dialyzer and upstream from the dialysate regeneration unit, wherein operation of the control pump in an efflux direction can cause net removal of fluid from the blood on an extracorporeal side of the membrane in the dialyzer to generate an ultrafiltrate. The ultrafiltrate can be added to the ultrafiltrate reservoir. Operation of the control pump in an influx direction causes net addition of fluid to the blood on the extracorporeal side of the membrane. The sodium concentration of an input fluid can be modified using a sodium management system through application of an electrical field to generate a sodium-modified fluid. The sodium modified input fluid can be either dialysate or ultrafiltrate, and the input fluid can be divided into first and second flow streams within the sodium management system. The sodium-modified fluid can be used to modify the dialysate.

In any embodiment, a method or system to control the sodium concentration of a dialysate can use electrodialysis.

In any embodiment, the method or system can be controlled compliant. In any embodiment, the method or system can have a closed, fixed volume.

In any embodiment, a control or ultrafiltration pump can be connected to an ultrafiltrate reservoir, which pumps fluid into or out of the dialysate flow loop at a position downstream from the dialyzer and upstream from the dialysate regeneration unit.

In any embodiment, operation of the control pump in an efflux direction causes net removal of fluid from the blood on the extracorporeal side of a membrane in the dialyzer to generate an ultrafiltrate, which can be added to the ultrafiltrate reservoir, and operation of the control pump in an influx direction causes net addition of fluid to the blood on the extracorporeal side of the membrane.

In any embodiment, a method or system to control the sodium concentration of a dialysate can use forward osmosis.

In any embodiment, a method or system to control the sodium ion concentration of a dialysate can use capacitive deionization.

In any embodiment, a method or system to control the sodium ion concentration of dialysate can modify the sodium concentration from the ultrafiltrate waste with reverse osmosis and uses the resulting sodium-modified fluid for sodium ion concentration adjustment to the dialysate.

In any embodiment, a method or system to control the sodium ion concentration of dialysate can modify the sodium concentration of ultrafiltrate using electrodialysis and uses the resulting sodium-modified fluid for sodium ion adjustment.

In any embodiment, a method or system to control the sodium ion concentration of a dialysate can modify the sodium concentration of ultrafiltrate with capacitive deionization and uses the resulting fluid for sodium ion adjustment.

In any embodiment, a method or system to control the sodium ion concentration of a dialysate can modify the sodium ion concentration from a stream coming from a dialysate or ultrafiltrate reservoir with reverse osmosis and can use the resulting fluid for sodium ion adjustment.

In any embodiment, a method or system to control the sodium ion concentration of a dialysate can modify the sodium ion concentration from a stream coming from a dialysate or ultrafiltrate reservoir with electrodialysis and can use the resulting fluid for sodium ion adjustment.

In any embodiment, a method or system to control the sodium ion concentration of a dialysate can modify the sodium concentration from a stream coming from a dialysate or ultrafiltrate reservoir with capacitive deionization and can use the resulting fluid for sodium ion adjustment.

In any embodiment, a methods or system for sodium ion concentration modification can provide for the addition of a sodium-modified fluid upstream or downstream from a dialysate regeneration unit.

BRIEF DESCRIPTION OF THE DRAWINGS

Throughout the figures and the specification, components with the same numbers in the FIG.'s refer to the same components.

DETAILED DESCRIPTION

Definitions

Figure 1:
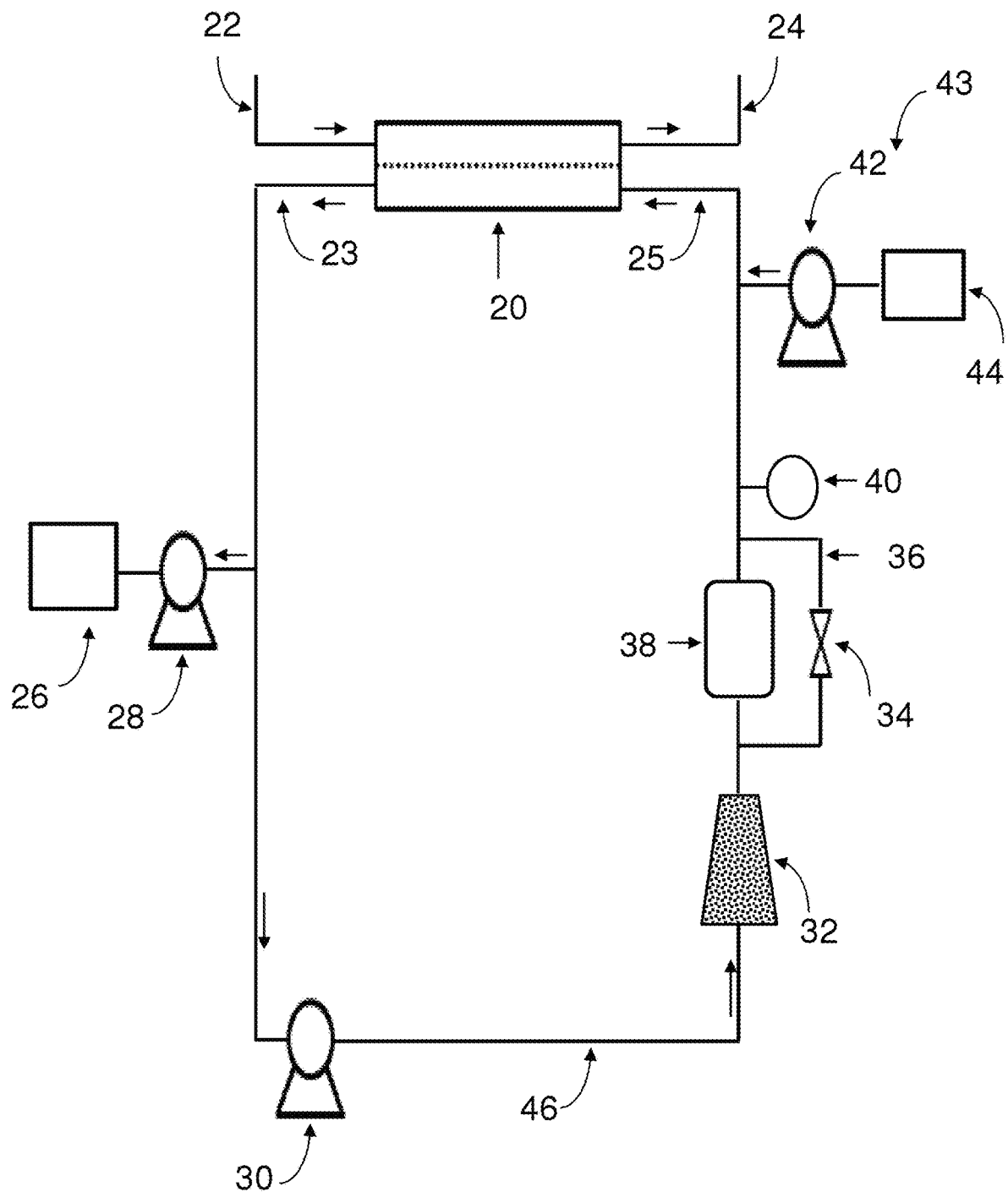
FIG. 1 is a flow diagram of a dialysate regeneration system with a controlled compliant dialysate circuit and a sodium management system.

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

The term "acid or base equivalents" refers to an equivalent acid or base donating or accepting an equal number of moles of hydrogen or hydronium ions per mole of the acid to which the equivalent acid is being equated, or mole of hydroxide ions to which the equivalent base is being equated.

The term "cation infusate pump" historically known as an "acid concentrate pump" in dialysis systems refers to a pump that serves the function to move or control the flow of a fluid to and/or from a reservoir having a substance that contains at least one cation species, such as calcium, magnesium and potassium ions. In the present invention, the historically used term of "acid concentrate pump" is used.

The term "acid feed" refers a state of fluid communication that enables an acid solution to be obtained from an acid source and connected or feed into a receiving source or flow path.

An "acid" can be either an Arrhenius acid, a Brønsted-Lowry acid, or a Lewis acid. The Arrhenius acids are substances or fluids which increase the concentration of hydronium ions (H3O+) in solution. The Brønsted-Lowry acid is a substance which can act as a proton donor. Lewis acids are electron-pair acceptors.

The term "activated carbon" may refer to a porous carbon material having a surface area greater than 500 m² per gram. Activated carbon can be capable of absorbing several species including heavy metals such as lead, mercury, arsenic, cadmium, chromium and thallium among others, oxidants such as chlorine and chloramines, fluoride ions, and waste species such as phosphate and certain nitrogen-containing waste species such as creatinine and uric acid.

The terms "administering," "administer," "delivering," "deliver," "introducing," and "introduce" can be used, in context, interchangeably to indicate the introduction of water or a dialysate having an altered concentration of at least one component, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane or other means.

The term "air trap" refers to a structure for separating a gas from a mixture of a gas and a liquid or any other separation means known in the art. An air trap can include a hydrophobic membrane for allowing gases to pass and for preventing the passage of water.

The term "albumin sieving coefficient" can be used to describe the amount of albumin that will cross a membrane.

The terms "ammonia sensing module" and "ammonia detector" refer to a unit that performs all or part of the function to detect a predetermined level of, or measure a concentration of, ammonia and/or ammonium ions in a fluid.

The term "anion exchange membrane" refers to a positively charged membrane, which allows negatively charged ions (anions) to pass through.

The term "anticoagulant" is a substance that prevents or delays the clotting of blood, such as heparin, Fragmin®, and sodium citrate.

The term "atmospheric pressure" refers to the local pressure of air in the environment in proximity to the system at the time that the system is operating.

The term "base concentrate pump" refers to a device that performs work on a fluid solution to cause fluid flow to control the volume transfer of a basic or alkaline solution into a circuit.

The term "base concentrate reservoir" refers to a vessel or container, optionally accessible by a pump that contains a variable amount of a basic or alkaline fluid solution.

The term "base module" refers to a basic unit of an apparatus for hemodialysis, hemodiafiltration, or hemofiltration that incorporates one or more fluid pathways. Exemplary, non-limiting components that can be included in the base module include conduits, valves, pumps, fluid connection ports, sensing devices, a controller and a user interface. The base module can be configured to interface with reusable or disposable modules of the apparatus for hemodialysis, hemodiafiltration, or hemofiltration to form at least one complete fluid circuit, such as a dialysis, cleaning, disinfection, priming or blood rinse back circuit.

A "base" can be either a substance that can accept hydrogen cations (protons) or more generally, donate a pair of valence electrons. A soluble base is referred to as an alkali if it contains and releases hydroxide ions (OH—) quantitatively. The Brønsted-Lowry theory defines bases as proton (hydrogen ion) acceptors, while the more general Lewis theory defines bases as electron pair donors, allowing other Lewis acids than protons to be included.[1] The Arrhenius bases act as hydroxide anions, which is strictly applicable only to alkali.

The term "base feed" refers a state of fluid communication that enables a base solution to be obtained from a base source and connected or feed into a receiving source or flow path.

The term "bicarbonate buffer component" refers to any composition contain bicarbonate (HCO3-) ion or a conjugate acid of bicarbonate ion in any amount, proportion or pH of the composition. The bicarbonate buffering system is an important buffer system in the acid-base homeostasis of living things, including humans. As a buffer, it tends to maintain a relatively constant plasma pH and counteract any force that would alter it. In this system, carbon dioxide (CO2) combines with water to form carbonic acid (H2CO3), which in turn rapidly dissociates to form hydrogen ions and bicarbonate (HCO3-) as shown in the reactions below. The carbon dioxide-carbonic acid equilibrium is catalyzed by the enzyme carbonic anhydrase; the carbonic acid-bicarbonate equilibrium is simple proton dissociation/association and needs no catalyst.

$$CO_2 + H_2O \leftrightarrows H_2CO_3 \leftrightarrows HCO_3^- + H^+$$

Any disturbance of the system will be compensated by a shift in the chemical equilibrium according to Le Chatelier's principle. For example, if one attempted to acidify the blood by dumping in an excess of hydrogen ions (acidemia), some of those hydrogen ions will associate with bicarbonate, forming carbonic acid, resulting in a smaller net increase of acidity than otherwise.

The term "bicarbonate buffer concentrate" refers to a bicarbonate ($HCO_3^-$) buffer component composition at a higher concentration than found at normal physiological levels that can be used to for instants to readjusted the pH of the dialysate (see also definition of bicarbonate buffer component relating to its use).

The term "bicarbonate cartridge" refers to a container that can be a stand-alone container or alternatively can be integrally formed with an apparatus for hemodialysis, hemodiafiltration, or hemofiltration. The bicarbonate cartridge can store a source of buffering material, such as sodium bicarbonate, and can be configured to interface with at least one other functional module found in systems for hemodialysis, hemodiafiltration, or hemofiltration. For example, the bicarbonate cartridge can contain at least one fluid pathway and include components such as conduits, valves, filters or fluid connection ports. The bicarbonate cartridge can be disposable or be consumable wherein the cartridge is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "bicarbonate feed" refers to fluid solution introduced into part of the dialysis or ultrafiltrate system. For example a "bicarbonate feed" is a conduit that contains a bicarbonate buffer concentrate that is used to readjust the pH of the dialysate.

The term "bidirectional pump" refers to a device configured to perform work on a fluid to cause the fluid to flow alternatively in either of two opposing directions.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "blood access connection" refers to a junction or aperture through which the blood of a subject is conveyed to or from an extracorporeal circuit. Commonly, the blood access connection is made between a terminal end of a conduit of an extracorporeal circuit and the terminal end of a catheter or fistula needle that is distal to the subject receiving therapy. A subject may have more than one blood access connection when receiving therapy. In the case of two blood access connections they can be referred to as an arterial blood access connection and a venous blood access connection.

The term "blood solute" refers to a substance dissolved, suspended, or present in blood or dialysate.

The term "bolus" refers to an increase (or at times a decrease) of limited duration in an amount or concentration of one or more solutes, for example sodium, glucose and potassium, or a solvent, for example water, such that the concentration of a solution is changed. The term "bolus" includes delivery of solute and/or solvent to the dialysate fluid path such that it is delivered to the blood of a subject via diffusion and/or convection across a dialysis membrane such that the amount or concentration in the subject is increased or decreased. A "bolus" may also be delivered directly to the extracorporeal flow path or the blood of a subject without first passing through the dialysis membrane.

The term "buffer conduit flow path" refers to a fluid flow path in fluid communication with a stored source of a buffering material, such as bicarbonate.

The term "buffer source" refers to a stored material, such as bicarbonate, acetate or lactate that provides buffering.

The terms "buffer source container" and "buffer source cartridge" refer to objects that have or hold one or more materials, in solid and/or solution form, that are a source of buffering, for example a bicarbonate, a lactate, or acetate; and the object further having at least one port or opening to allow at least a portion of the buffering material to be released from the object during operation of the system.

The term "blood based solute monitoring system" refers to a system for monitoring a substance dissolved or suspended or present in blood or dialysate.

The term "blood rinse back" refers to returning the blood from a dialyzer and/or extracorporeal circuit to a subject, normally at conclusion of a therapy session and prior to disconnecting or removing the subject's blood access connection or connections. The procedure can include conveying a physiologically compatible solution through the extracorporeal circuit to push or flush the blood from the extracorporeal circuit to the subject via the subject's blood access connection or connections.

The terms "bypass circuit" "bypass conduit," "bypass flow path," "bypass conduit flow path" and "bypass" refer to a component or collection of components configured or operable to create an alternate fluid pathway to convey a fluid around one or more other components of a fluid circuit such that at least a portion of the fluid does not contact or pass through the one or more other components. At times the term "shunt" may be used interchangeable with the term "bypass." When any of the above "bypass" terms listed in this paragraph are used in context as being part of a controlled compliant system, then the relevant referenced "bypass" has the proper characteristics as to operate within a controlled compliant system as defined herein.

The term "bypass regulator" refers to a component such as valve that can determine the amount of fluid that can pass through a by-pass portion of a fluid circuit.

The term "cartridge" refers to a compartment or collection of compartments that contains at least one material used for operation of the system of the present invention.

The term "cassette" refers to a grouping of components that are arranged together for attachment to, or use with the device, apparatus, or system. One or more components in a cassette can be any combination of single use, disposable, consumable, replaceable, or durable items or materials.

The term "cation exchange membrane" refers to a negatively charged membrane, which allows positively charged ions (cations) to pass. By convention, electrical current flows from the anode to the cathode when a potential is applied to an electrodialysis cell. Negatively charged anions such as chloride ions are drawn towards the anode, and positively charged cations such as sodium ions are drawn towards the cathode.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "cation concentrate reservoir" refers to an object having or holding a substance that is comprised of at least one cation, for example calcium, magnesium, or potassium ions.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "conduit," "conduit" or "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "chronic kidney disease" (CKD) refers to a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The term "citric acid" refers to an organic acid having the chemical formula $C_6H_8O_7$, and may include anhydrous and hydrous forms of the molecule, and aqueous solutions containing the molecule.

The term "cleaning and/or disinfection concentrate" refers to a dry substance, or concentrated solutions containing at least one material for use in cleaning and/or disinfection of an apparatus.

The term "cleaning and/or disinfection solution" refers to a fluid that is used for the purpose of removing, destroying or impairing at least a portion of at least one contaminant. The contaminant may be organic, inorganic or an organism. The fluid may accomplish the purpose by transmission of thermal energy, by chemical means, flow friction or any combination thereof.

The terms "cleaning manifold" and "cleaning and disinfection manifold" refer to an apparatus that has fluid connection ports and one or more fluid pathways, or fluid port jumpers, that, when connected to jumpered ports of a base module, create one or more pathways for fluid to be conveyed between the jumpered ports of the base module. A cleaning manifold may be further comprised of additional elements, for example valves and reservoirs.

The term "container" as used herein is a receptacle that may be flexible or inflexible for holding fluid or solid, such as for example a spent dialysate fluid, or a sodium chloride or sodium bicarbonate solution or solid.

The terms "common container," "common cartridge," or "common reservoir," and the like refer to an object or apparatus that can hold more than one material; however, the time of holding more than one material may or may not necessarily be at the same time. The material(s) may be in solid and/or solution forms and may be held in separate compartments within the object or apparatus.

The term "common fluid inlet port" refers to an opening or aperture through which all fluid first passes to enter an object, apparatus or assembly.

The term "common fluid outlet port" refers to an opening or aperture through which all fluid passes to exit an object, apparatus or assembly.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "component" and "components" refer to a part or element of a larger set or system. As used herein, a component may be an individual element, or it may itself be a grouping of components that are configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

The term "concentrate pump" refers to a device that can perform work on a fluid solution to cause the fluid flow and can actively control the transfer of fluid volume such as an infusate or an acid concentrate, base concentrate, or buffer concentrate into a circuit.

The terms "concentrate flow channel," "concentrate flow loop," "concentrate stream," refer to a fluid line in which ion concentration is increased during electrodialysis.

The terms "conditioning conduit flow path" and "conditioning flow path" refer to a fluid pathway, circuit or flow loop that incorporates a source of a conditioning material, for example a sodium salt or bicarbonate.

The term "conditioning flow path inlet" refers to a location on a conditioning flow path where fluid enters the conditioning flow path The term "conditioning flow path outlet" refers to a location on a conditioning flow path where fluid exits the conditioning flow path.

The terms "conductivity meter," "conductivity sensor," "conductivity detector," conductivity electrode or the like, refer, in context, to a device for measuring the electrical conductance of a solution and/or the ion, such as a sodium ion, concentration of a solution. In specific examples, the conductivity sensor, meter, or conductor can be directed to a specific ion such as sodium and be referred to as a "sodium electrode," "sodium sensor," "sodium detector," or "sodium meter."

The term "conductive species" refers to a material's ability to conduct an electric current. Electrolytes are an example of a conductive species in dialysate fluids, such as, but not limited to the presence sodium, potassium, magnesium, phosphate, and chloride ions. A fluid's ability to conduct an electrical current is due in large part to the ions present in the solution. A fluid's ability to conduct an electrical current is due in large part to the ions present in the solution.

The terms "conduit," "circuit," and "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "consumables" refers to components that are dissipated, wasted, spent or used up during the performance of any function in the present invention. Examples include a quantity of sodium, bicarbonate, electrolytes, infusates, sorbents, cleaning and disinfecting ingredients, anticoagulants, and components for one or more concentrate solutions.

The terms "consumables cartridge" and "consumables container" refer to an object or apparatus having or holding one or more materials that are depleted during operation of the system. The one or more materials may be in solid and/or solution form and can be in separate compartments of the object or apparatus. The object or apparatus may be single use, or may be replenished and used multiple times, for example, by refilling the object to replace the consumed material.

The terms "contact," "contacted," and "contacting" refers, in context, to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding fluid or solid, such as for example a spent dialysate fluid, or a sodium chloride or sodium bicarbonate solution or solid, or the like.

The term "contaminant" refers to an undesirable or unwanted substance or organism that may cause impairment of the health of a subject receiving a treatment or of the operation of the system.

The term "control pump," such as for example an "ultrafiltrate pump," refers to a pump that is operable to pump fluid bi-directionally to actively control the transfer of fluid volume into or out of a compartment or circuit.

The terms "control reservoir," "ultrafiltrate reservoir," "solution reservoir," "therapy solution reservoir," and "waste reservoir," as the case may be, refers, in context, to a vessel or container, optionally accessible by a control pump that contains a variable amount of fluid, including fluid that can be referred to as an ultrafiltrate. These reservoirs can function as a common reservoir to store fluid volume from multiple sources in a system. Other fluids that can be contained by these reservoirs include, for example, water, priming fluids, waste fluids, dialysate, including spent dialysate, and mixtures thereof. In certain embodiments, the reservoirs can be substantially inflexible, or non-flexible. In other embodiments, the reservoirs can be flexible containers such as a polymer bag.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

A "control system" consists of combinations of components that act together to maintain a system to a desired set of performance specifications. The control system can use processors, memory and computer components configured to interoperate to maintain the desired performance specifications. It can also include fluid control components, and solute control components as known within the art to maintain the performance specifications.

The terms "control valve" and "valve" refer to a device that can be operated to regulate the flow of fluid through a conduit or flow path by selectively permitting fluid flow, preventing fluid flow, modifying the rate of fluid flow, or selectively guiding a fluid flow to pass from one conduit or flow path to one or more other conduits or flow paths.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if the patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/ or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, and as discussed herein and shown in the drawings is that the controlled compliant system can move fluids bi-directionally. In certain cases, the bi-directional fluid movement is across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

The term "convective clearance" refers to the movement of solute molecules or ions across a semi-permeable barrier due to force created by solvent molecules moving across the semi-permeable barrier.

The terms "controller," "control unit," "processor," and "microprocessor" refers, in context, to a device which monitors and affects the operational conditions of a given system. The operational conditions are typically referred to as output variables of the system wherein the output variables can be affected by adjusting certain input variables.

The terms "coordinately operates" and "coordinately operating" refer to controlling the function of two or more elements or devices so that the combined functioning of the two or more elements or devices accomplishes a desired result. The term does not exclusively imply that all such elements or devices are simultaneously energized.

The term "deaeration" refers to removing some or all of the air contained in a liquid including both dissolved and non-dissolved air contained in the liquid.

The terms "de-aeration flow path" and "de-aeration flow path" refer to a set of elements that are configured in fluid communication along a fluid flow pathway such that a liquid can be passed through the fluid flow pathway to accomplish removal of some or all of the air or gas contained in the liquid, including removal of air or gas that is dissolved in the liquid.

The terms "degas module" and "degassing module" refer to a component that separates and removes any portion of one or more dissolved or undissolved gas from a liquid. A degas module can include a hydrophobic membrane for allowing ingress or egress of gases through a surface of the module while preventing the passage of liquid through that surface of the module.

The term "deionization resin" refers to any type of resin or material that can exchange one type of ion for another. In one specific case, the term can refer to the removal of ions such as potassium, magnesium, sodium and calcium in exchange for hydrogen and/or hydroxide ions.

The term "detachable" refers to a characteristic of an object or apparatus that permits it to be removed and/or disconnected from another object or apparatus.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is ~140 mEq/L. Normal blood sodium levels range from approximately 135 mEq/L to 145 mEq/L. The REDY system typically uses dialysate ranging from 120 mEq/L to 160 mEq/L. In certain embodiment, a "predetermined limit" or "predetermined concentration" of sodium values can be based off the common sodium levels for dialysate and normal blood sodium levels. "Normal" saline at 0/9% by weight and commonly used for priming dialyzers and extracorporeal circuits is 154 mEq/L.

The terms "dialysate flow loop," "dialysate flow path," and "dialysate conduit flow path" refers, in context, to a fluid pathway that conveys a dialysate and is configured to form at least part of a fluid circuit for hemodialysis, hemofiltration, hemodiafiltration or ultrafiltration.

The terms "dialysate regeneration unit" and "dialysate regeneration system" refer to a system for removing certain electrolytes and waste species including urea from a dialysate after contact with a dialyzer. In certain instances, the component contained within the "dialysate regeneration unit" or "dialysate regeneration system" can decrease the concentration or conductivity of at least one ionic species, or release and/or absorb at least one solute from a dialysate.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," and generally "membrane," refer, in context, to a semi-permeable barrier selective to allow diffusion and convection of solutes of a specific range of molecular weights through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Diffusive permeability" is a property of a membrane describing permeation by diffusion. Diffusion is the process of solutes moving from an area of higher concentration to an area of lower concentration.

The terms "diluate flow channel," "feed stream," "diluate stream," and the like, refer, in context, to a fluid line of solution entering an electrodialysis cell or electrodialysis unit wherein the ion concentration in the fluid solution is changed.

The terms "diluent" and "diluate" refer to a fluid having a concentration of a specific species less than a fluid to which the diluent is added.

A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode refers" to a rod electrode with a small diameter. Other electrode and electrode head geometries can be considered.

The term "disinfection fluid" refers to a solution for use in cleaning and disinfecting an apparatus for hemodialysis, hemodiafiltration or hemofiltration. The disinfection fluid may act thermally, chemically, and combinations thereof to inhibit growth of or to destroy microorganisms. The "disinfection fluid" may further act to remove, at least in part, a buildup of microorganisms on a surface of a fluid flow path, such buildups of microorganisms may be commonly referred to as a biofilm.

The terms "diverted sample stream" and "diverting a sample stream" refer redirecting part of a fluid from the main flow path to accomplish another purpose, such as to measure a fluid characteristic, remove a portion of the fluid stream in order to take a sample. More than one sample stream may be diverted, such as a "first sample stream, "second sample stream," "third sample stream," "fourth sample stream," and the like.

The term "dry" as applied to a solid or a powder contained in a cartridge means not visibly wet, and may refer interchangeably to anhydrous and also to partially hydrated forms of those materials, for example, monohydrates and dihydrates.

The term "downstream" refers to a direction in which a moving dialysate or other fluid moves within a conduit or flow path.

The term "downstream conductivity" refers to the conductivity of a fluid solution as measured at a location of a fluid flow path in the direction of the normal fluid flow from a reference point.

The term "drain connection" refers to being joined in fluid communication with a conduit or vessel that can accept fluid egress from the system.

The term "dry composition" refers to a compound that does not contain a substantial quantity of water and can include anhydrous forms as well as hydrates for example, monohydrates and dihydrates.

The term "effluent dialysate," as used herein describes the discharge or outflow after the dialysate has been used for dialysis.

The term "electrode" as used herein describes an electrical conductor used to make contact with a nonmetallic part of a circuit, such as electrical conductors used to contact the fluids of the invention (e.g. dialysate) and to measure the conductivity of the fluid.

The term "electrode" as used herein describes an electrical conductor used to make contact with a part of a fluid, a solid or solution. For example, electrical conductors can be used as electrodes to contact any fluid (e.g. dialysate) to measure the conductivity of the fluid or deliver or receive charge to the fluid. A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode" refers to a rod electrode with a small diameter. Other electrode and electrode head geometries can be considered.

The term "electrode array" refers to an array of one or more electrodes contained in an insulator substrate. The insulator substrate can be rigid or flexible and acts to isolate the electrodes from each other. A non-limiting example of an "electrode array" is a flex-circuit, which is a flexible circuit board containing electrodes.

The term "electrode head" refers to the portion of an electrode that is in physical contact with a fluid, that conductivity is to be measured from.

The terms "electrode rinse" and "electrode rinse solution" refer to any suitable solution such as sodium sulfate solution that prevents undesirable oxidation and flushes reactants from an electrode surface.

The terms "electrode rinse flow channel," "electrode rinse stream," and the like refer to a fluid line of an electrode rinse or "electrode rinse solution."

The term "electrode rinse reservoir" refers to a vessel or container for holding the electrode rinse or electrode rinse solution. The reservoir may have an inflexible or flexible volume capacity.

The term "electrodialysis" refers to an electrically driven membrane separation process capable of separating, purifying, and concentrating desired ions from aqueous solutions or solvents.

The term "electrodialysis cell" refers to an apparatus having alternating anion- and cation-exchange membranes that can perform electrodialysis using an electrical driving force between an anode and cathode housed at opposite ends of the cell. The cell consists of a diluate compartment fed by a diluate stream and a concentrate compartment fed by a concentrate stream. One or more electrodialysis cells can be multiply arranged to form an "electrodialysis stack."

The term "electrolyte" refers to an ion or ions dissolved in an aqueous medium, including but not limited to sodium, potassium, calcium, magnesium, acetate, bicarbonate, and chloride.

The terms "electrolyte source" and "electrolyte source" refer to a stored substance that provides one or more electrolytes.

The terms "equilibrated," "equilibrate," "to equilibrate," and the like, refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more gases coming into equilibrium where the gases have equal pressures or between a liquid and a gas.

The term "equilibrated to the solute species concentration" refers to more specifically where a concentration of a particular solute species in a first fluid has become approximately equal to the concentration of that solute species in the second fluid. The concentration need not be exact.

The terms "evacuation volume," "priming volume" and "void volume" refer to the internal volume of a component or collection of components comprising a fluid flow path and are the volume of fluid that can be removed from the fluid flow path to empty the fluid flow path if it has been filled with fluid.

The term "extracorporeal," as used herein generally means situated or occurring outside the body.

The term "extracorporeal circuit" refers to a fluid pathway incorporating one or more components such as, but not limited to, conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

The term "feed solution" refers to a dialysate or ultrafiltrate fluid solution introduced into part of the dialysis or ultrafiltrate system. For example a "feed solution" can refer to a dialysate or ultrafiltrate fluid solution introduced to an electrodialysis cell.

The term "filtering media" refers to a material that can allow a fluid to pass through, but which inhibits passage of non-fluid substances that are larger than a predetermined size.

The terms "filtrate regeneration unit" and "filtrate regeneration system" refer to a system for removing certain electrolytes and waste species including urea from a filtrate produced using filtration.

The terms "filtrate regeneration circuit," "filtrate regeneration loop," and the like, refer to a flow path containing fluid resulting from filtration; for the removal of certain electrolytes and waste species including urea.

The term "filtration" refers to a process of separating solutes from a fluid, by passing the fluid through a filter medium across which certain solutes or suspensions cannot pass. Filtration is driven by the pressure difference across the membrane.

The term "first terminal end" of a flow path refers to one end of the flow path and "second terminal end" refers to another end of the flow path. Neither the "first terminal end" nor the "second terminal end" has any limitation on placement on an arterial or venous side.

The term "first terminal valve" refers to a valve substantially located at one end of a first fluid conduit without any requirement that the valve be place on an arterial or venous side. Similarly, the term "second terminal valve" refers to a valve substantially located at one end of a second fluid conduit and so on without any limitation on placement on an arterial or venous side.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that it recirculates, or passes the same position more than once as it moves through a flow loop. A flow loop may operate to cause fluid volume ingress to and fluid volume egress from the flow loop. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably.

The terms "flow restriction," "flow restriction device" and "flow restrictor" refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, a narrowing, or a simple length of tubing with flow cross section that produces the desired pressure drop when the fluid flows through it, such tubing being essentially rigid or compliant. Non-limiting examples of active flow restrictors are pinch valves, gate valves and variable orifice valves.

The term "flow stream" refers to fluid moving along a flow path

The term "fluid balance control pump" refers to where a control pump is used to adjust the concentration or amount of a solute or fluid in the system. For example, a fluid balance control pump is used for selectively metering in or selectively metering out a designated fluid wherein the concentration or amount of a solute or fluid is adjusted.

The term "fluid characteristic" refers to any chemical or biological components that make up or can be found dissolved or suspended in the fluid or gas properties associated with the fluid; or to any physical property of the fluid including, but not limited to temperature, pressure, general or specific conductivities associated with the fluid or related gases.

The term "fluid communication" refers to the ability of fluid to move from one component or compartment to another within a system or the state of being connected, such that fluid can move by pressure differences from one portion that is connected to another portion.

The term "flush reservoir" is used to describe a container that can accept or store fluid that is removed from the system during rinsing or cleaning of fluid pathways of the system, including draining the system after cleaning and/or disinfection has been completed.

"Hemodiafiltration" is a therapy that combines hemofiltration and hemodialysis.

"Hemofiltration" is a therapy in which blood is filtered across a semi-permeable membrane. Water and solutes are removed from the blood via pressure-driven convection across the membrane. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

The term "hemofilter" refers to a apparatus (or may refer to a filter) used in hemofiltration. A hemofilter apparatus can be connected to an extracorporeal circuit and configured to operate with a semipermeable membrane that separates at least a portion of the fluid volume from blood to produce a filtrate fluid.

The term "hydrophobic membrane" refers to a semipermeable porous material that may allow gas phases of matter to pass through, but which substantially resists the flow of water through the material due to the surface interaction between the water and the hydrophobic material.

"Hemodiafiltration" is a therapy that combines hemofiltration and hemodialysis.

The term "in contact" as referred to herein denotes (a) a coming together or touching, as of objects or surfaces; or (b) the state or condition of touching or of being in immediate proximity. "In contact" also includes fluids that are "in fluid communication with" with a solid, such as for example, a fluid, like a dialysate, in contact with a material layer of a sorbent cartridge, or a fluid in contact with a sensor.

The terms "infusate container" and "infusate reservoir" refer to a vessel, which can be substantially inflexible or non-flexible for holding a solution of one or more salts for the adjustment of the composition of a dialysate.

The term "infusate solution" refers to a solution of one or more salts for the adjustment of the composition of a dialysate, such as salts of calcium, magnesium, potassium, and glucose.

The term "infusate system" refers to a system that incorporates at least one fluid pathway including components such as conduits, valves, pumps or fluid connection ports, an infusate container or a controller configured to add an infusate solution to the dialysate.

The term "interchangeable bicarbonate cartridge" refers to a bicarbonate cartridge that can be configured for removal and replacement with a like bicarbonate cartridge. Interchangeable bicarbonate cartridges can be single use disposable, or re-fillable, re-usable containers.

The term "interchangeable sodium chloride cartridge" refers to a sodium chloride cartridge that can be configured for removal and replacement with a like sodium chloride cartridge. Interchangeable sodium chloride cartridges can be single use disposable, or re-fillable, re-usable containers.

The terms "introduce" and "introducing" refer to causing a substance to become present where it was not present, or to cause the amount or concentration of a substance to be increased.

The term "ion-exchange material" refers to any type of resin or material that can exchange one type of ion for another. The "ion-exchange material" can include anion and cation exchange materials. In one specific case, the term can refer to the removal of ions such as potassium, magnesium, sodium, phosphate and calcium in exchange for other ions such as potassium, sodium, acetate, hydrogen and/or hydroxide.

An "ion-exchange resin" or "ion-exchange polymer" is an insoluble matrix (or support structure) that can be in the form of small (1-2 mm diameter) beads, fabricated from an organic polymer substrate. The material has a developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions. In one specific case, the term can refer to the removal of ions such as potassium, magnesium, sodium, phosphate and calcium in exchange for other ions such as potassium, sodium, acetate, hydrogen and/or hydroxide.

The term "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The term "junction" refers to a common point of connection between two or more flow paths or conduits that allows a liquid and/or a gas to move from one pathway or conduit to another. A junction may be a reversible connection that can be separated when transfer of a liquid and/or gas between the flow paths or conduits is not needed.

The term "kidney replacement therapy" as used herein describes the use of a provided system to replace, supplement, or augment the function of a patient with impaired kidney function, such as would occur for a patient with Chronic Kidney Disease. Examples of kidney replacement therapy would include dialysis, hemofiltration, hemodialysis, hemodiafiltration, peritoneal dialysis, and the like.

The terms "luer connector" and "luer adapter" refer to adapters or connectors conforming to International Standards Organization (ISO) standards 594-2.

The term "manifold" refers to a collection of one or more fluid pathways that are formed within a single unit or subassembly. Many types of manifolds can be used, e.g. a cleaning and/or disinfecting manifold is used to clean or disinfect the defined flow loop when the flow loop is connected to the cleaning and/or disinfecting manifold.

The term "material layer" refers to the layers of materials found in a sorbent cartridge. The material layers in a sorbent cartridge may have one or more layers selected from a urease-containing material, alumina, zirconium phosphate, zirconium oxide, and activated carbon.

The term "memory" refers to a device for recording digital information that can be accessed by a microprocessor, such as RAM, Dynamic RAM, microprocessor cache, FLASH memory, or memory card.

The term "mesh electrode" refers to an electrode in the shape of a mesh, where a mesh consists of a planar structure with openings. The mesh can be made from; overlapping wires or strips, a sheet machined or manufactured to contain holes or openings, or a sheet with a permeable, porous structure. In all cases the mesh is manufactured from materials that result in electrodes, such as titanium, platinum, stainless steel, and iridium. In the case of an electrode mesh consisting of overlapping wires or strips, certain wires or strips can be isolated from other wires or strips with an insulator material in order to apply one polarity to certain wires or strips and the opposite polarity to other wires or strips.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "mid-weight uremic wastes" refers to uremic wastes that can pass through a dialysis membrane and have a molecular weight less than about 66,000 g/mol and greater than about 1000 g/mol. An example of a middle molecule is beta-2 microglobulin.

The term "mixing chamber" refers to a chamber or vessel, with one or more inlet and outlet fluid streams, that provides mixing between the fluid streams entering the chamber.

The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow loop in a controlled compliant system.

A multiplexer" or "mux" is an electronic device that selects one of several analog or digital input signals and forwards the selected input into a single line.

The term "nitrogenous waste" refers to any non-polymeric nitrogen-containing organic compound originating from the blood of a patient. Nitrogenous waste includes urea and creatinine, which are both "waste species."

The term "one-way valve" refers to a device that allows flow to pass in one direction through the valve, but prevents or substantially resists flow through the valve in the opposite direction. Such devices can include devices commonly referred to as check valves "Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "parallel or wound hollow fiber assembly" refers to any device that incorporates a porous or non-porous hollow fiber material that allows a gas to pass through the material wall of the hollow fibers, but resists the passage of a liquid through the material wall and is configured as multiple strands aligned in parallel or wrapped around a core. The liquid to be degassed may be conveyed through either the inside of the hollow fibers or around the outside of the hollow fibers. Optionally, a gas may be conveyed on the side of the material wall that is opposite the liquid to be degassed. Optionally, a vacuum may be applied on the side of the material wall that is opposite the liquid to be degassed.

A "patient" or "subject" is a member of any animal species, preferably a mammalian species, optionally a human. The subject can be an apparently healthy individual, an individual suffering from a disease, or an individual being treated for a disease.

The term "parallel to a central axis" refers to the position of components, e.g. sensors that can be placed in a plane having portions generally parallel to the central axis.

The terms "pathway," "conveyance pathway" and "flow path" refer to the route through which a fluid, such as dialysate or blood travels.

The term "patient fluid balance" refers to the amount or volume of fluid added to or removed from a subject undergoing a treatment.

The term "peristaltic pump" refers to a pump that operates by compression of a flexible conduit or tube through which the fluid to be pumped passes.

The term "perpendicular to a central axis" refers to the position of components, e.g. sensors that can be placed in a plane having portions generally perpendicular to the central axis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

The term "pH-buffer modifying solution" refers to a solution that can reduce the acidity (pH) of the working dialysate solution when added to the dialysate The term "pH-buffer sensor" refers to a device for measuring the acidity or basicity (pH) and the buffer concentration of the dialysate solution.

The term "pH-buffer management system" refers to a system managing the pH and buffer concentration of a dialysate by adding, removing or generating a fluid to the dialysate such that the dialysate is modified by the pH-buffer management system to have a different pH and buffer concentration.

The term "pH-buffer measurement system" refers to a system measuring the pH and/or buffer concentration of a dialysate or fluid within the system.

The terms "portable system" and "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The term "potable water" refers to drinking water or water that is generally safe for human consumption with low risk of immediate or long term harm. The level of safety for human consumption can depend on a particular geography where water safe for human consumption may be different from water considered safe in another jurisdiction. The term does not necessarily include water that is completely free of impurities, contaminants, pathogens or toxins. Other types of water suitable for use in the present invention can include purified, deionized, distilled, bottled drinking water, or other pre-processed water that would be understood by those of ordinary skill in the art as being suitable for use in dialysis.

The term "potassium-modified fluid" refers to fluid having a different conductivity or potassium concentration compared to a second fluid to which the potassium-modified fluid is added to modify the conductivity or potassium concentration of the second fluid.

The terms "physiologically compatible fluid" and "physiological compatible solution" refer to a fluid that can be safely introduced into the bloodstream of a living subject.

The term "plumbing," as used herein generally describes any system of valves, conduits, channels, and lines for supplying any of the fluids used in the invention.

The term "porosity," as used herein describes the fraction of open pore volume of a membrane.

The terms "pressure differential" and "pressure drop" refer to the difference in pressure measurements of a fluid between two points of measurement.

The terms "pressure meter" and "pressure sensor" refer to a device for measuring the pressure of a gas or liquid in a vessel or container.

The terms "priming process" and "priming" refer to the process of conveying a liquid into the void volume of a fluid pathway to fill the pathway with liquid.

The term "priming volume" refers to the volume of priming fluid required to fill the void volume of the subject pathway, device, or component, as the particular case may be.

The term "priming overflow reservoir" refers to a reservoir which during priming is used to collect the overflow of fluid during the priming process.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pump" refers to any device that causes the movement of fluids or gases by the application of suction or pressure.

The term "pulsatile pump" refers to a pump where the pumped fluid undergoes periodic variation in velocity and/or pressure.

The terms "reconstitute" and "reconstituting" refer to creating a solution by addition of a liquid to a dry material or to a solution of higher concentration to change the concentration level of the solution. A "reconstitution system" in one use, is a system that rebalances the dialysate in the system to ensure it contains the appropriate amount of electrolytes and buffer.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "shunt," as most often used herein describes a passage between channels, in the described filtration and purification systems, wherein the shunt diverts or permits flow from one pathway or region to another. An alternate meaning of "shunt" can refer to a pathway or passage by which a bodily fluid (such as blood) is diverted from one channel, circulatory path, or part to another. The term "bypass" can often be used interchangeably with the term "shunt."

The term "sodium-concentrate solution" refers to a solution having a high concentration of sodium ions relative to another solution or fluid.

The terms "sodium chloride cartridge" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. For example, the sodium chloride cartridge or container can contain at least one fluid pathway and include components such as conduits, valves, filters or fluid connection ports.

The term "regenerative capacity of the sorbent" refers to the remaining capacity for the sorbent cartridge or a particular material layer of the sorbent cartridge to perform its intended function.

The term "regenerative substance" refers to a sorbent material contained in a "regeneration module." The term "first chosen regenerative substance," as used in the present invention refers to a particular regenerative substance, identified as "first chosen regenerative substance." The term "second chosen regenerative substance" refers to a particular regenerative substance, identified as "second chosen regenerative substance."

The term "regeneration module" refers to an enclosure having one or more sorbent materials for removing specific solutes from solution, such as urea. In certain embodiments, the term "regeneration module" includes configurations where at least some of the materials contained in the module do not act by mechanisms of adsorption or absorption.

The terms "remnant volume" and "residual volume" refer to the volume of fluid remaining in a fluid flow path after the fluid flow path has been partially emptied or evacuated.

The terms "replacement fluid" and "substitution fluid" refer to fluid that is delivered to the blood of a subject undergoing convective renal replacement therapies such as hemofiltration or hemodiafiltration in order to replace at least a portion of the fluid volume that is removed from the subject's blood when the blood is passed through a hemofilter or a dialyzer.

The term "reserve for bolus infusion" refers to an amount of solution available, if needed, for the purpose of administering fluid to a subject receiving therapy, for example, to treat an episode of intradialytic hypotension.

The term "reusable" refers to an item that is used more than once. Reusable does not imply infinitely durable. A reusable item may be replaced or discarded after one or more use.

The term "reverse osmosis" refers to a filtration method of forcing a solvent from a region of high solute concentration through a semipermeable membrane to a region of low solute concentration by applying a pressure in excess of osmotic pressure. To be "selective," this membrane should not allow large molecules or ions through the pores (holes), but should allow smaller components of the solution (such as the solvent) to pass freely.

The term "reverse osmosis rejection fraction" refers to the resulting solute that is retained on the pressurized side of the membrane and the pure solvent is allowed to pass to the other side in a reverse osmosis system.

The term "reversible connections" refers to any type of detachable, permanent or non-permanent connection configured for multiple uses.

The term "salination pump" refers to a pump configured to move fluid and/or control movement of fluid through a conditioning flow path, such as through or from a source of a conditioning material such as sodium chloride or sodium bicarbonate.

The term "salination valve" refers to a valve configured to control the flow of fluid in a conditioning flow path, such as through or from a source of a conditioning material such as sodium chloride or sodium bicarbonate.

The term "segment" refers to a portion of the whole, such as a portion of a fluid flow path or a portion of a fluid circuit. A segment is not limited to a tube or conduit, and includes any grouping of elements that are described for a particular segment. Use of the term "segment," by itself, does not imply reversible or detachable connection to another segment. In any embodiment, a segment may be permanently connected to one or more other segments or removably or detachably connected to one or more segments.

The terms "selectively meter fluid in" and "selectively meter fluid out" generally refer to a process for controllably transferring fluids from one fluid compartment (e.g. a selected patient fluid volume, flow path, or reservoir) to another fluid compartment. One non-limiting example is where a control pump may transfer a defined fluid volume container, reservoirs, flow paths, conduit of the controlled compliant system. When fluid is moved from a reservoir into another part of the system, the process is referred to as "selectively metering fluid in" as related to that part of the system. Similarly, one non-limiting example of removing a defined volume of dialysate from a dialysate flow path in a controlled compliant system and storing the spent dialysate in a control reservoir, can be referred to as "selectively metering-out" the fluid from the dialysate flow path.

The terms "semipermeable membrane," "selectively permeable membrane," "partially permeable membrane," and "differentially permeable membrane," refer to a membrane that will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight. For example, Dialyzer membranes come with different pore sizes. Those with smaller pore size are called "low-flux" and those with larger pore sizes are called "high-flux." Some larger molecules, such as beta-2-microglobulin, are not effectively removed with low-flux dialyzers. Because beta-2-microglobulin is a large molecule, with a molecular weight of about 11,600 daltons, it does not pass effectively through low-flux dialysis membranes.

The term "sensor," which can also be referred to as a "detector" in certain instances, as used herein can be a converter that measures a physical quantity of a matter in a solution, liquid or gas, and can convert it into a signal which can be read by an electronic instrument.

The term "sensor element" refers to a device or component of a system that detects or measures a physical property. The terms "sodium management system" and "sodium management" broadly refer to a system or process that can maintain the sodium ion concentration of a fluid in a desired range. In certain instances, the desired range can be within a physiologically-compatible range. The sodium ion concentration of an input solution can be modified by any means including application of an electrical field.

The term "sodium-modified fluid" refers to fluid having a different conductivity or sodium concentration compared to a second fluid to which the sodium-modified fluid is added to modify the conductivity or sodium concentration of the second fluid.

The term "sodium conduit flow path" refers to a flow path in fluid communication with a sodium chloride cartridge which then can pump saturated sodium solution into the dialysate by pumping and metering action of a salination pump.

The term "sodium source" refers to a source from which sodium can be obtained. For example, the sodium source can be a solution containing sodium chloride or a dry sodium chloride composition that is hydrated by the system.

The term "solid potassium" refers to a solid composition containing a salt of potassium such as potassium chloride at any purity level. In general, the solid potassium will be easily soluble in water to form a solution.

The term "solid sodium" refers to a solid composition containing a salt of sodium such as sodium chloride at any purity level. In general, the solid potassium will be easily soluble in water to form a solution and of high purity.

The term "solid bicarbonate" refers to a composition containing a salt of bicarbonate such as sodium bicarbonate at any purity level. In general, the solid bicarbonate will be easily soluble in water to form a solution.

The term "solute" refers to a substance dissolved, suspended, or present in another substance, usually the component of a solution present in the lesser amount.

The terms "sorbent cartridge" and "sorbent container" refer to a cartridge containing one or more sorbent materials for removing specific solutes from solution, such as urea. "Sorbent cartridge" includes configurations where at least some of the materials contained in the cartridge do not act by mechanisms of adsorption or absorption.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "source of cations" refers a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid. Non-limiting examples include glucose, dextrose, acetic acid and citric acid.

The term "specified gas membrane permeability" refers to a determined rate at which a gas membrane will allow a gas to pass through the membrane from a first surface to a second surface, the rate being proportional to the difference in absolute pressure of the gas in proximity to the first side of the membrane and in proximity to the second side of the membrane.

The term "spent dialysate" refers to a dialysate that has been contacted with blood through a dialysis membrane and contains one or more impurity, or waste species, or waste substance, such as urea.

The term "static mixer" refers to a device that mixes two or more component materials in a fluid solution without requiring the use of moving parts.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

The term "tap water" refers to water, as defined herein, from a piped supply.

The term "temperature sensor" refers to a device that detects or measures the degree or intensity of heat present in a substance, object, or fluid.

A "therapy solution reservoir" refers to any container or reservoir that holds a physiological compatible fluid.

The term "total bicarbonate buffer concentration" refers to the total concentration of bicarbonate ($HCO_3^-$) ion and a conjugate acid of bicarbonate in a solution or composition.

A "therapy solution reservoir" refers to any container or reservoir that holds a physiological compatible fluid.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "uremic wastes" refers to a milieu of substances found in patients with end-stage renal disease, including urea, creatinine, beta-2-microglobulin.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, a hemodiafiltration, or a filtration process.

The terms "unbuffered sodium bicarbonate" or "solution of unbuffered sodium bicarbonate" refer to a sodium bicarbonate composition that is not buffered with a conjugate acid or base in any amount, proportion or pH adjustment.

The term "upstream" refers to a direction opposite to the direction of travel of a moving dialysate or other fluid within a conduit or flow path.

The term "urea sensor" refers to a device for measuring or allowing for the calculation of urea content of a solution. The "urea sensor" can include devices measuring urease breakdown of urea and measurement of the resulting ammonium concentration. The sensing methods can be based on any one of conductimetric, potentiometric, thermometric, magnetoinductic, optical methods, combinations thereof and other methods known to those of skill in the art.

The term "vacuum" refers to an action that results from application of a pressure that is less than atmospheric pressure, or negative to the reference fluid or gas.

The term "vent" as referred to in relationship to a gas, refers to permitting the escape of a gas from an defined portion of the system, such as, for example, as would be found in the degassing module.

The term "void volume" refers to a specific volume that can be occupied by a fluid in a defined space such as a dialysate circuit of the invention including all components contained therein.

The terms "waste species," "waste products" and "impurity species" refers to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "working dialysate solution" refers to a dialysate solution that is undergoing active circulation or movement through a system including conduits, pathways, dialyzers and cartridges.

Sodium Management Systems

In one aspect, the invention is directed toward a system having a dialysate regeneration system and a sodium management system for adjusting the sodium ion concentration of a dialysate. In certain embodiments, the sodium management system modifies the sodium ion concentration of an input solution through the application of an electric field to generate a sodium-modified fluid that has a sodium concentration greater or lesser than the dialysate. The sodium-modified fluid can then be added to the dialysate in a dialysate flow path to modify the sodium ion concentration of the dialysate. As such, systems and methods are provided to modify the sodium ion concentration and/or conductivity of a dialysate to allow for a fixed volume, or a non-fixed volume, of working dialysate to be regenerated to a physiological-compatible composition for dialysis treatment.

FIG. 1 depicts a dialysis system having a blood path and a dialysate regeneration path separated by a dialyzer 20. The blood enters the dialyzer 20 through a flow line inlet 22 and exits through a flow line outlet 24. The dialysate regeneration circuit shown in FIG. 1 can have either a flow loop 46 that is controlled compliant, or a flow loop that does not display the controlled compliant properties as defined herein. In certain embodiments of the invention (not shown), the dialysis systems may also have a non-compliant volume as defined herein. The dialysate solution is recirculated with a dialysate pump 30 and allowed to flow through a dialysate regeneration unit 32 and a sodium management system 38.

Figure 15:
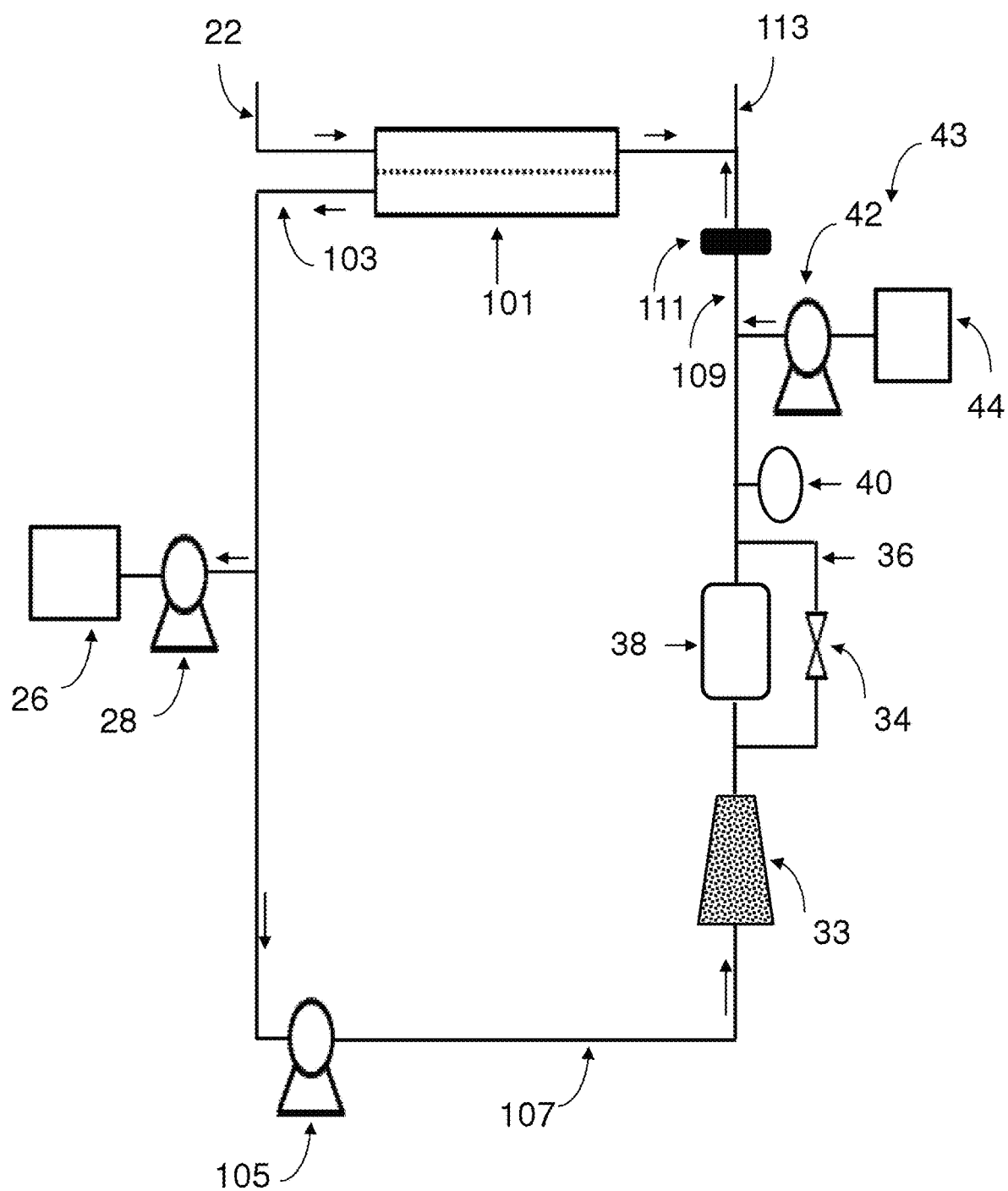
FIG. 15 is a flow diagram of a hemofiltration regeneration system with a controlled compliant filtration circuit and a sodium management system.

The dialysate regeneration unit 32 or filtrate regeneration unit 33 of FIG. 15 consists of components or materials that are capable of removing solutes from the dialysate including: urea, phosphate, calcium, magnesium, potassium, creatinine, uric acid, beta-2-microglobulin and sulfate. The dialysate regeneration unit 32 or filtrate regeneration unit 33 may also contain components or materials that release or bind sodium during the process of removing solutes from the dialysate. For example, the dialysate regeneration unit 32 or filtrate regeneration unit 33 may consist of a sorbent cartridge containing activated carbon, urease, zirconium phosphate and hydrous zirconium oxide, similar to the sorbent cartridge used in the "REDY" system. It is noted that the regenerated dialysate produced by REDY systems is subject to variations in pH and sodium concentrations non-conducive to physiological norms.

The dialysate exiting the dialysate regeneration unit 32 flows through a sodium management system 38 and/or a by-pass loop 36, regulated by a by-pass regulator 34. The by-pass regulator 34 determines the amount of dialysate that passes through the sodium management system 38. The by-pass regulator 34 could consist of a pinch valve, on/off valve, or a valve with a range of open conditions such as a needle valve. The sodium management system 38 acts to remove or add sodium to the dialysate. The sodium management system 38 and by-pass loop 36 may be placed anywhere along flow loop 46, but preferably immediately after the dialysate regeneration unit 32. Because the dialysate regeneration unit 32 removes waste species from the dialysate, including urea, and electrolytes, such as potassium ions, magnesium ions, etc., the sodium management system 38 acts mainly on the removal or modification of sodium. Therefore, the size and power requirements for the sodium management system 38 can be minimized. As shown in FIG. 1 the sodium management system is placed after the dialysate regeneration system 32, which allows effective control of sodium concentration before returning fluid to the dialyzer 20. However, by placing the sodium management system before the dialysate regeneration unit 32, the dilution or removal of sodium in some cases will also remove waste products from the dialysate, reducing the capacity requirements of the dialysate regeneration unit 32. In certain embodiments the use of the by-pass loop 36 is not necessary if the sodium management system 38 actively controls the amount of sodium modification performed. For example, in certain embodiments removal of the by-pass loop 36 in FIG. 1 or closing valve 34 will result in all of the dialysate flowing through the sodium management system 38. The sodium management system 38 can adjust the amount of sodium added or removed from the dialysate based on system needs as described herein to maintain acceptable levels of sodium concentration.

After passing through the sodium management system 38 or by-pass loop 36 the dialysate flow passes a sodium sensor or conductivity sensor 40. As used herein, a sodium sensor refers to a device that gives an indication of sodium ion concentration or an indication of overall conductivity of a fluid or solution. The sodium sensor 40 measures the amount of sodium in the dialysate at that point and may be used to control the operation of the sodium management system and the by-pass regulator 34. The sodium sensor 40 may consist of an ionselective electrode, conductivity monitor, or other suitable sensor technology for measuring sodium in aqueous solutions. The sodium sensor 40 may also be connected anywhere along the dialysate flow loop 46.

Blood circulating through the dialyzer 20 via an extracorporeal circuit exchanges waste components with dialysate circulating through the dialyzer 20 and dialysate flow loop 46. Waste species including ions and uremic toxins, such as uric acid, creatinine, and β2-microglobin, and urea diffuse from the blood to the dialysate within the dialyzer 20 via a semipermeable membrane contained therein.

Regeneration of the dialysate within the dialysate flow loop 46 can be achieved through contacting the dialysate with sorbents contained within the dialysate regeneration unit 32. Examples of useful sorbent materials include the REDY sorbent system and U.S. Pat. Nos. 3,669,880; 3,989,622; 4,581,141; 4,460,555; 4,650,587; 3,850,835; 6,627,164; 6,818,196; and 7,566,432 and U.S. Patent Publications 2010/007838; 2010/0084330; and 2010/0078381 and International Patent Publication WO 2009/157877 A1, which are incorporated herein by reference. In some embodiments, the dialysate regeneration unit 32 can contain three or four different kinds of materials selected from the group: 1) a urease-containing material, where urease is an enzyme that catalyzes the conversion of urea to ammonium ions and carbon dioxide; 2) a zirconium phosphate (ZrP) material that has the capacity to act as a cation exchanger by absorbing a large quantity of ammonium ions in exchange for sodium and hydrogen ions; 3) a zirconium oxide material $(ZrO)_x$, namely hydrous zirconium oxide, which acts as an anion exchanger by exchanging phosphate for acetate; and 4) an activated carbon material that has a surface area for adsorption of a wide range of impurities including metal ions and uremic toxins, such as uric acid, creatinine, and β2-microglobin. However, there is no limitation on the minimum number of kinds of materials used in the dialysate regeneration unit 32 wherein the unit can contain any one or two of the materials disclosed herein. In some embodiments, the zirconium phosphate material can be replaced with a magnesium phosphate material.

The principal waste species removed during treatment of a patient is urea that accumulates in the blood of individuals with various degrees of kidney disease or impairment. Since urea is an electrically neutral species, the dialysate regeneration unit 32 or filtrate regeneration unit 33 can convert urea to a charged ammonium species that can then be removed from the dialysate before the dialysate exits the regeneration unit 32. In certain embodiments, the ammonium may be removed by an ion exchange material prior to exiting the dialysate regeneration unit 32. However, in order to maintain electrical neutrality, the removal of charged ammonium species has to be matched by exchange with another charged species, which is sodium ion in certain embodiments. As such, the concentration of sodium ions can increase over time in the absence of operation of the sodium management system 38.

As further shown in FIG. 1, after the sodium sensor 40, the dialysate flow passes a reconstitution system 43 consisting of an infusate pump 42 and an infusate reservoir 44. The purpose of the reconstitution system 43 is to rebalance the dialysate to ensure it contains the appropriate amount of electrolytes and buffer. The infusate reservoir 44 may contain multiple reservoirs each containing specific compounds. For example the infusate reservoir 44 may consist of a reservoir containing a concentrated electrolyte solution such as calcium acetate, magnesium acetate, potassium acetate and concentrated acid solution such as acetic acid or citric acid. The infusate reservoir 44 may also consist of an additional reservoir containing a concentrated buffer solution such as sodium bicarbonate or sodium lactate. Multiple reconstitution systems 43 may be used with the dialysis system shown in FIG. 1. In some embodiments, the infusate reservoir 44 does not contain a substantial quantity or concentration of sodium ions.

In any embodiment, the solution provided by the reconstitution system 43 does not necessarily contain a substantial concentration or amount of sodium ions. That is, sodium ions for the purpose of increasing the sodium concentration of the dialysate in the dialysate flow loop 46 are not necessarily provided for by the reconstitution system 43.

Regenerated dialysate 25 passes through the dialyzer 20 and exits as waste dialysate 23. The waste dialysate 23 flow passes an ultrafiltration unit that consists of an ultrafiltration pump 28 and ultrafiltration reservoir 26. The ultrafiltration pump 28 removes fluid from the dialysate loop 46 and because of the dialysate loop's 46 controlled compliance, fluid is drawn across dialyzer 20 from the blood. The ultrafiltrate system acts to remove ultrafiltrate from the patient and remove any fluid volume added in along the dialysate loop 46, such as fluid from the reconstitution system 43. The fluid removed by ultrafiltrate pump 28 is collected in the ultrafiltrate reservoir 26.

In certain embodiments, the components of the dialysate flow loop 46 can have a controlled compliant volume. As such, fluid is in passive equilibrium from flowing from the extracorporeal circuit to the dialysate flow loop 46 due to the controlled compliant volume of the dialysate loop 46 and volume of fluids within the system (which includes attached reservoirs). The net balance of fluid is prevented from passively flowing between the flow loop 46 to the extracorporeal circuit via the dialyzer 20 since such a movement of fluid will leave a vacuum in the flow loop 48 or require the flow loop 46 to contract. Since the dialyzer can be a high-flux type that readily allows for the passage of water, there is some fluid flux back and forth across the dialyzer membrane due to the pressure differential on the blood and dialysate sides of the membrane. This is a localized phenomenon due to the low pressure required to move solution across the membrane and is called backfiltration, however, this results in no net fluid gain or loss by the patient.

The components forming the dialysate flow loop 46 can have a controlled compliant volume wherein the dialysate flow loop 46 further incorporates a control or ultrafiltration pump 28 that can be operated bi-directionally to cause the net movement of fluid from an extracorporeal side of the dialyzer 20 into the dialysis flow loop 46 or to cause net movement of fluid from the dialysate flow loop 46 into the extracorporeal side of the dialyzer 20. In particular, the control or ultrafiltration pump 28 is operated in the efflux direction to cause the movement of fluid from the extracorporeal side of the dialyzer 20 into the dialysis flow loop 46 and in the influx direction to cause the movement of fluid from the dialysis flow loop 46 into the extracorporeal side of the dialyzer 20. The action of typical pumps contemplated by the invention function by expanding or contracting a space wherein any suitable type of pump can be used in the present invention.

In certain embodiments, operation of the control or ultrafiltration pump 28 in the influx direction can be substituted with operation of the infusate pump 42 to drive liquid from the infusate reservoir 44 into the dialysis flow loop 46 and subsequently cause movement of fluid from the dialysis flow loop 46 to the extracorporeal side of the dialyzer 20. The control or ultrafiltration pump 28 can also be used for the movement of fluid in the opposite direction across the dialyzer 20 into the dialysis flow loop 46. It is noted that the infusate reservoir 44 or ultrafiltrate reservoir 26 can allow the system to adjust the patient fluid volume by withdrawing fluid and storing the desired amount in the respective reservoir and/or by providing rebalanced fluids to the patient and removing waste products. For example, the fluid stored in a control reservoir attached to the dialysate circuit can be used to store a volume of fluid equal to the ultrafiltrate volume removed from the patient during ultrafiltration (UF). Alternatively, the fluid stored in the control reservoir can be an infusate delivered to the patient. In certain embodiments, the delivered fluid can contain a therapeutic component deliverable across the dialyzer 20 and into the patient's bloodstream. Additionally, the volume of the dialysate flow loop 46 can be actively controlled by the user or a programmed controller.

The control or ultrafiltration pump 28 allows for fluid to move from the dialysate flow loop 46 to the extracorporeal side without creating a vacuum, wherein the operation of the control pump 28 is controlled as described herein. Likewise, the control pump 28 allows for fluid to move from the extracorporeal side, and hence the patient's body via the action of the control pump 28. Movement of fluid between the extracorporeal side of the dialyzer 20 and the dialysate flow loop 46 can be accurately controlled and metered using the removed fluid in certain embodiments. In other embodiments, the removed fluid can be transferred back to the patient through dialysate flow loop 46 using the ultrafiltrate stored in ultrafiltration reservoir 26. In some embodiments, the ultrafiltration reservoir 26 can be prefilled with water, dialysate or other fluid for addition to the dialysate flow loop 46 and/or for use or treatment within the sodium control system 38.

As such, some embodiments have a controlled compliant dialysate flow loop 46 that can be accurately controlled to precisely remove or add fluid to the extracorporeal side of the dialyzer 20. Due to the substantially inflexible void volume of the conduits, the dialysate regeneration unit 32 and other components of the dialysate flow loop 46, the net movement of fluid over any time interval across the dialysate membrane within the dialyzer 20 can be accurately controlled by creating a means to accurately introduce or remove fluid from the patient. This capability can further be used to enhance the convective clearance of the system for uremic impurities while controlling the net fluid removed from the patient, for example, creating periods of fluid movement across the membrane with occasional reversal of direction. In certain embodiments, an ultrafiltrate can be used as described herein. However, the present invention is not limited to a controlled compliant system. As such, the dialysate flow loop 46 in certain embodiments is not a controlled compliant system and may include one or more open reservoir for storing or accumulating dialysate.

In certain embodiments, an ultrafiltration pump 28 can be a peristaltic pump, a volumetric metering pump, diaphragm pump, or a syringe style pump. Hence, the dialysate flow loop 46 has a substantially inflexible volume that can deliver controlled changes in volume modulated by the control or ultrafiltration pump 28, the infusion pump 42 and optionally any other pump(s) that add or remove fluid to and from the dialysate flow loop 46. The contents of U.S. patent application Ser. No. 13/565,733 filed on Aug. 2, 2012 are incorporated herein by references in their totality.

In certain embodiments, the dialysate flow loop 46 has a void volume from about 0.15 L to about 0.5 L. In other embodiments, the dialysate flow loop 46 has a void volume from about 0.2 L to about 0.4 L or from 0.2 L to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 L to about 5 L, and micro-volumes from as small as 0.1 L to about 0.5 L such as 0.1 L to 0.2 L, 0.1 L to 0.3 L, 0.1 L to 0.4 L, 0.2 L to 0.3 L, 0.3 L to 0.4 L, or 0.3 L to 0.5 L are contemplated by the invention.

Configuration of Sodium Management System

Figure 2:
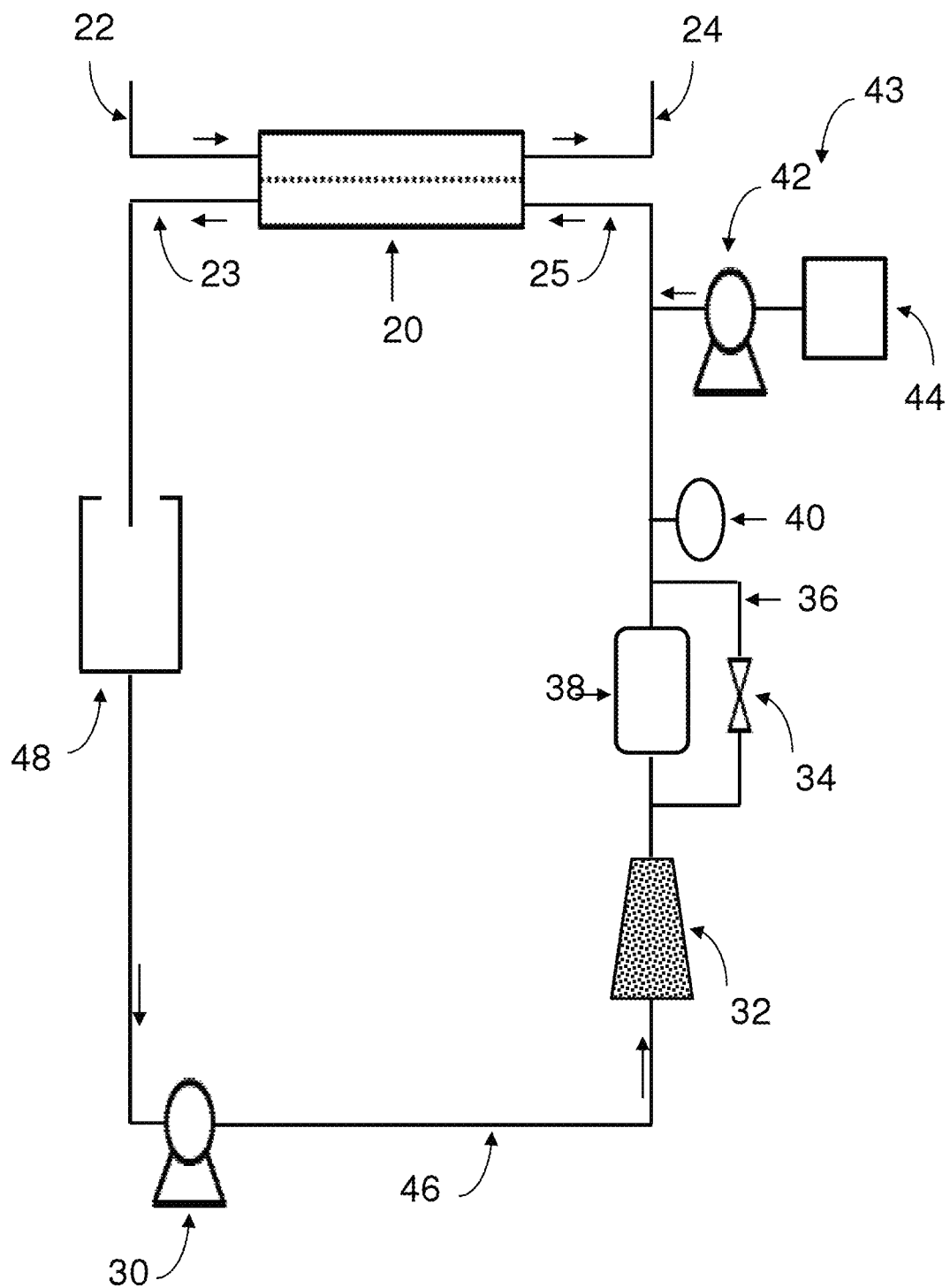
FIG. 2 is a flow diagram of a dialysate regeneration system with an open, non-fixed volume dialysate circuit and a sodium management system.

FIG. 2 is an example of a dialysis system similar to that shown in FIG. 1. However, the dialysate flow loop 46 shown in FIG. 2 includes a dialysate reservoir 48. Dialysate reservoir 48 is a variable volume reservoir. The dialysate fluid contained in dialysate reservoir 48 can vary during the course of a hemodialysis run. Specifically, the volume will increase as ultrafiltrate is removed from the patient by filtration across dialyzer 20. For use with the variable volume reservoir 48 of FIG. 2, ultrafiltration may be controlled by any one of balance chambers and an ultrafiltration (UF) metering pump, duplex metering pumps and a UF metering pump, and transmembrane pressure regulators with mass or volume measurement (not shown). Components with the same numbers in the FIG.'s refer to the same components. As used herein, the term ultrafiltrate includes fluid contained in the dialysate reservoir 48.

Figure 3:
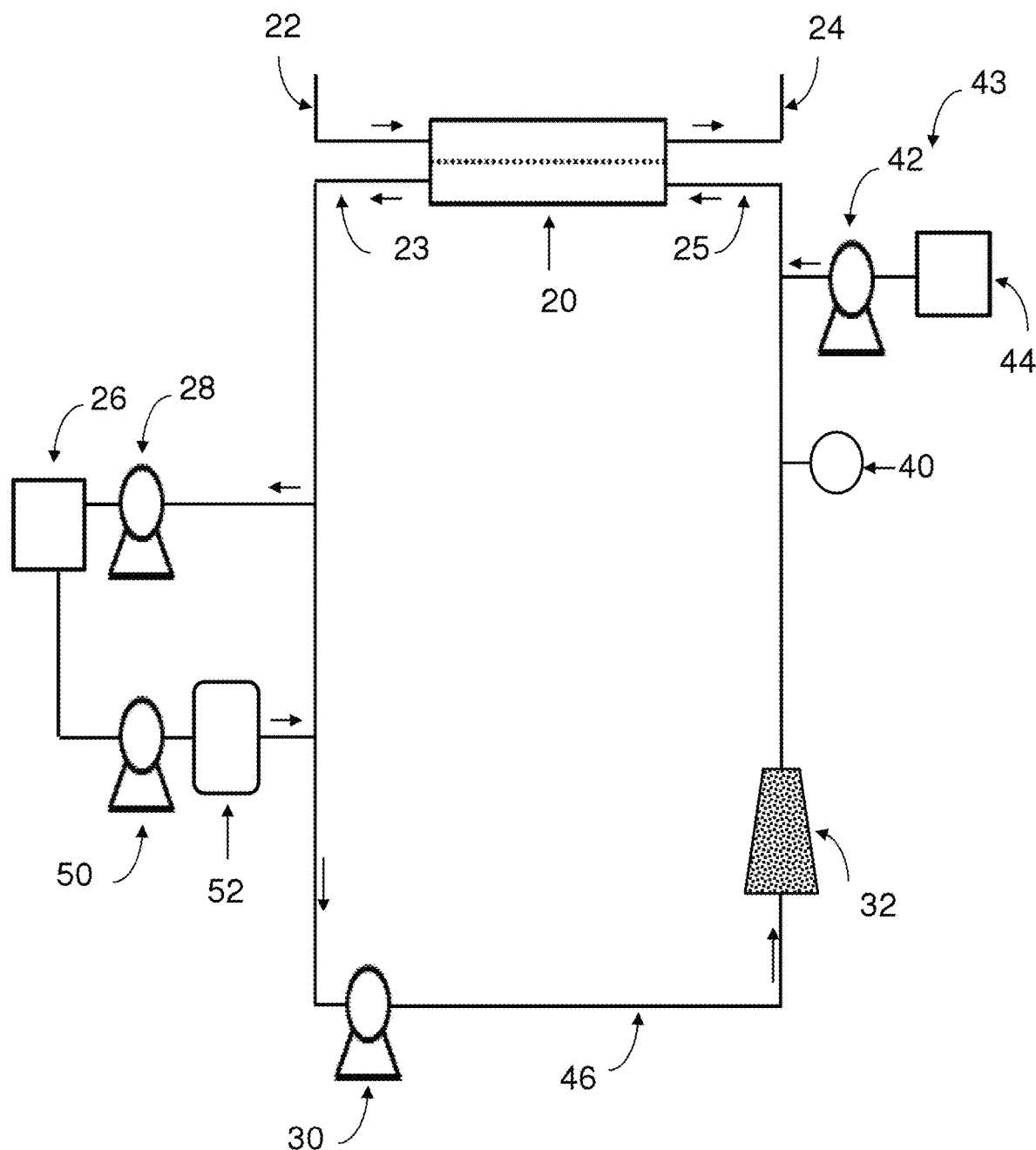
FIG. 3 is a flow diagram of a dialysate regeneration system with a controlled compliant dialysate circuit and a sodium management system utilizing ultrafiltrate waste to generate a sodium modifying fluid delivered before a dialysate regeneration unit.
Figure 4:
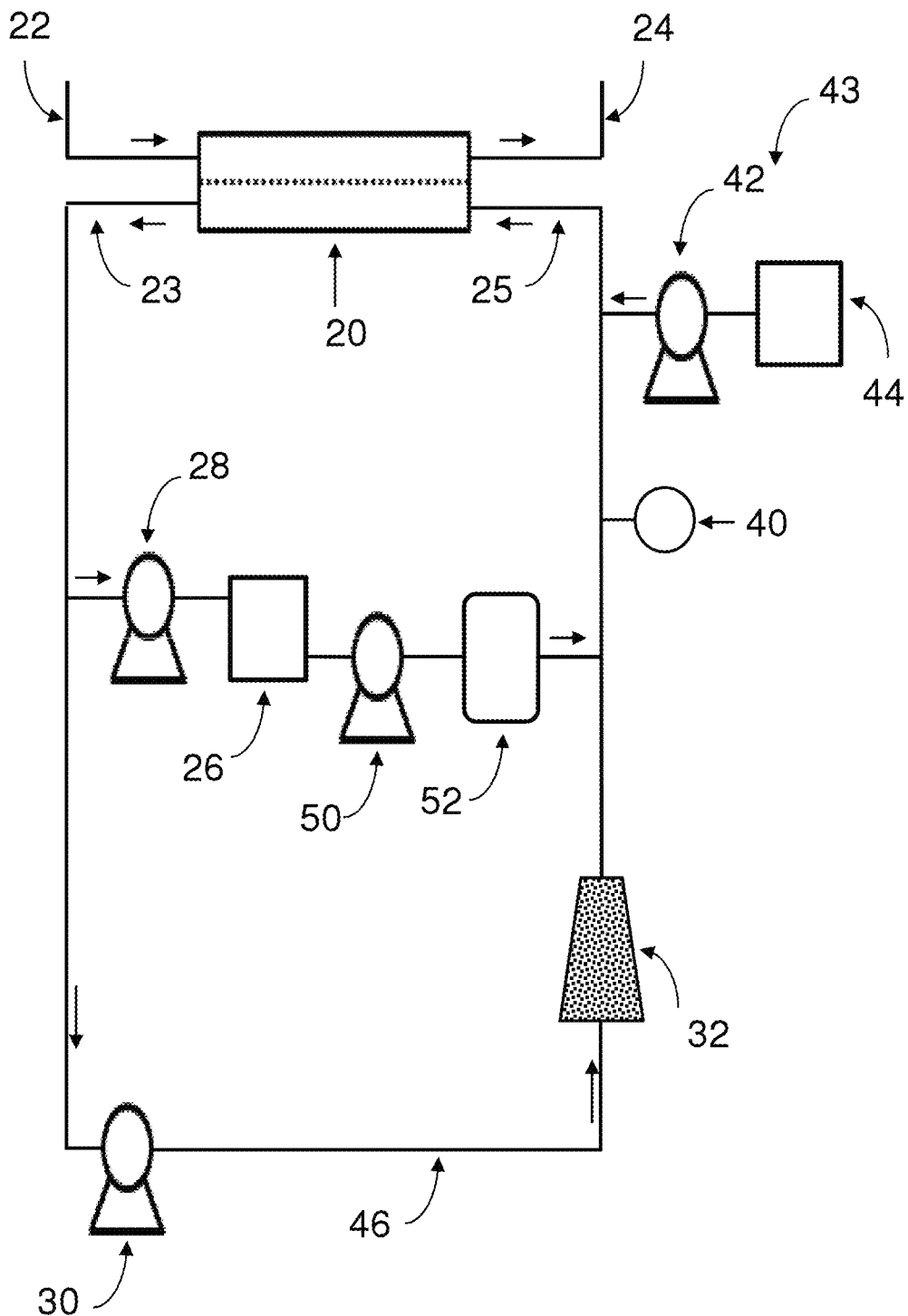
FIG. 4 is a flow diagram of a dialysate regeneration system with a controlled compliant dialysate circuit and a sodium management system utilizing ultrafiltrate waste to generate a sodium modifying fluid delivered after a dialysate regeneration unit.

FIGS. 3 and 4 show flow diagrams for a dialysis system with a controlled compliant dialysate flow loop 46 and a sodium management system. In other embodiments, the system may be a non-compliant system or non-expandable system that resists the introduction of a volume of fluid after air has been removed from a defined space such as a vessel, conduit, container, pathway or cartridge. The ultrafiltrate that is collected in the ultrafiltrate reservoir 26 is pumped through a sodium management system 52 with a sodium management pump 50 and returned to the dialysate flow loop 46 to act as a sodium modifying solution. The sodium management system 52 is structurally equivalent to the sodium management system 38 described above. However, movement of fluid, and hence volume of fluid, through the sodium management system 52 is controlled by a sodium management pump 50 rather than a by-pass regulator 34. The sodium-modified solution generated by the sodium management system 52 or system 38 has a sodium ion concentration that is greater than or lesser than the sodium ion concentration of the dialysate present in and/or circulating in dialysate flow loop 46. As such, the addition of the generated sodium-modified fluid to the dialysate flow loop 46 adjusts the concentration of sodium ions in the dialysate circulating in the dialysate flow loop 46 to keep the sodium ion concentration within a predetermined range. In some embodiments, the dialysate is adjusted by addition of a sodium-modified fluid to maintain conductivity of the dialysate within the flow loop 46 to be between about 12.6 to about 15.4 mS/cm.

In some embodiments, the dialysate within the flow loop 46 is directly treated by the sodium management system 52 or 38 and returned to the flow loop 46 as a sodium-modified solution to adjust sodium ion concentration. In other embodiments, the sodium management system 52 or 38 may reduce or increase the sodium concentration of the ultrafiltrate waste solution. As described above, ultrafiltration or control pump 28 can remove fluid from the dialysate flow loop 46 for storage in the ultrafiltration reservoir 26 of FIG. 1. Operation of the ultrafiltration pump 28 to add fluid to ultrafiltration reservoir 26, as described above, causes a net removal of fluid from the blood across the membrane of the dialyzer 20. Alternatively, the ultrafiltration reservoir 26 can be prefilled with a solution. The fluid or solution stored in the ultrafiltration reservoir 26 can be diverted to sodium management system 52 to generate a sodium-modified fluid as necessary for adjustment of sodium ion concentration within the dialysate flow loop 46.

As described in more detail below, a sodium management system 38, or any other sodium management system, can provide a sodium-modified solution having a higher sodium ion concentration than the dialysate in the dialysate flow loop 46. As such, the sodium management system 38 can function to increase the sodium concentration of the dialysate. In certain embodiments, any sodium ions added to the dialysate increase the concentration of sodium ions using sodium ions stored in the sodium management system and selectively released into the sodium-modified solution through the modulation of an electrical field. An increase in the sodium ion concentration of the dialysate is not achieved through the introduction of an infusate solution containing sodium ions provided from outside of the sodium management system 38 and/or added to the dialysate flow loop 46 by means of a pump or other appropriate metering device. That is, the generation of a sodium-modified solution having a sodium ion concentration for increasing the sodium ion concentration of a dialysate is accomplished through modulation of an electrical field and not through the addition of a separately-prepared infusate solution. Those skilled in the art will understand that the addition of an infusate solution by reconstitution system 44 can decrease the sodium ion concentration of the dialysate depending upon the volume of solution added by the reconstitution system 43.

FIG. 3 shows a flow diagram for addition of the sodium-modified fluid generated from fluid in the ultrafiltration reservoir 26 to the dialysate flow loop 46 prior or upstream to the dialysate regeneration system 32. Reservoir 26 can optionally hold a small volume of fluid that can be used for system priming, dialysis therapy, provision of fluid bolus, blood rinse back and system cleaning and disinfection via pumps 28 or 50.

Movement of fluid through the sodium management system 52 to the flow loop 46 can be controlled by sodium management pump 50. FIG. 4 shows a flow diagram for addition of the sodium-modified fluid generated from fluid in the ultrafiltration reservoir 26 to the dialysate flow loop 46 after or downstream from the dialysate regeneration system 32. Reservoir 26 holds a small volume of fluid that can be used for system priming, dialysis therapy, provision of fluid bolus, blood rinse back and system cleaning and disinfection via pumps 28 or 50. In practice, the ultrafiltration reservoir 26 can be filled during the start-up and priming of the system with a fluid of desired composition. For example, water can be added to the ultrafiltration reservoir 26 to aid in dilution of the ultrafiltrate and require less removal by the sodium management system 52. Where the water added to ultrafiltration reservoir 26 is not chemically and microbiologically pure or otherwise suitable for use in the system, the inflow to dialysate loop 46 must occur prior to the regeneration unit 32. It is noted that the sodium-modified fluid generated from fluid in the ultrafiltration reservoir 26 will generally contain waste species and electrolytes including urea, creatinine, calcium, magnesium, and potassium. Some of these species will be removed by the sodium management system 52. It is expected that the concentration of waste species and electrolytes will be low in the sodium-modified fluid. Therefore, addition of the sodium-modified fluid after the dialysate regeneration unit 32 will not have deleterious effects on the dialysis therapy.

Figure 5:
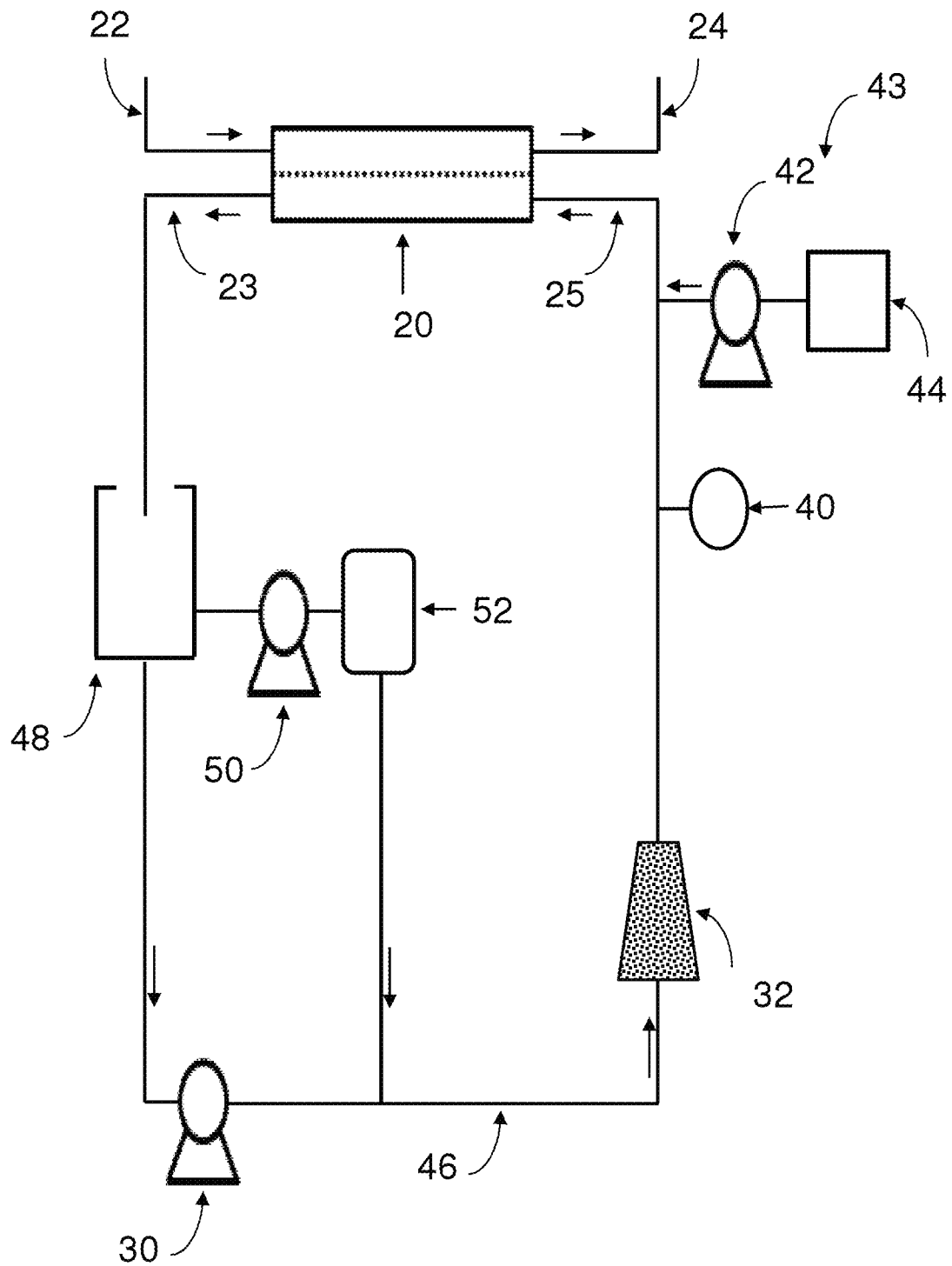
FIG. 5 is a flow diagram of a dialysate regeneration system with an open, non-fixed volume dialysate circuit and a sodium management system utilizing dialysate from a dialysate reservoir to generate a sodium modifying fluid delivered after a dialysate regeneration unit.

FIG. 5 shows a flow diagram for a dialysis system consisting of a dialysate flow loop 46 that includes a variable volume dialysate reservoir 48, similar to the flow diagram shown in FIG. 2. The flow diagram of FIG. 5 also includes a sodium management pump 50 that draws fluid from the dialysate reservoir 48 and passes it through a sodium management system 52 that acts to modify the sodium concentration of the draw solution from the dialysate reservoir 48. The solution that is drawn from the dialysate reservoir 48 and modified in sodium concentration is then returned back to the dialysate flow loop 46. As shown in FIG. 5, the solution is returned before or upstream from the dialysate regeneration system 32; however, the fluid can also be returned after or downstream from the dialysate regeneration system 32. After the dialysate regeneration system 32, the dialysate flow passes a reconstitution system 43 consisting of an infusate pump 42 and an infusate reservoir 44. The reconstitution system 43 rebalances the dialysate to ensure the fluid contains an appropriate amount of electrolytes and buffer. The infusate reservoir 44 may contain multiple reservoirs each containing specific compounds. For example the infusate reservoir 44 may consist of a reservoir containing a concentrated electrolyte solution such as calcium acetate, magnesium acetate, potassium acetate and concentrated acid solution such as acetic acid or citric acid. The infusate reservoir 44 may also consist of an additional reservoir containing a concentrated buffer solution such as sodium bicarbonate or sodium lactate. Multiple reconstitution systems 43 may be used with the dialysis system shown in FIG. 5. In some embodiments, the infusate reservoir 44 does not contain a substantial quantity or concentration of sodium ions. In any embodiment, the solution provided by the reconstitution system 43 does not necessarily contain a substantial concentration or amount of sodium ions. That is, sodium ions for the purpose of increasing the sodium concentration of the dialysate in the dialysate flow loop 46 are not necessarily provided for by the reconstitution system 43.

Figure 6:
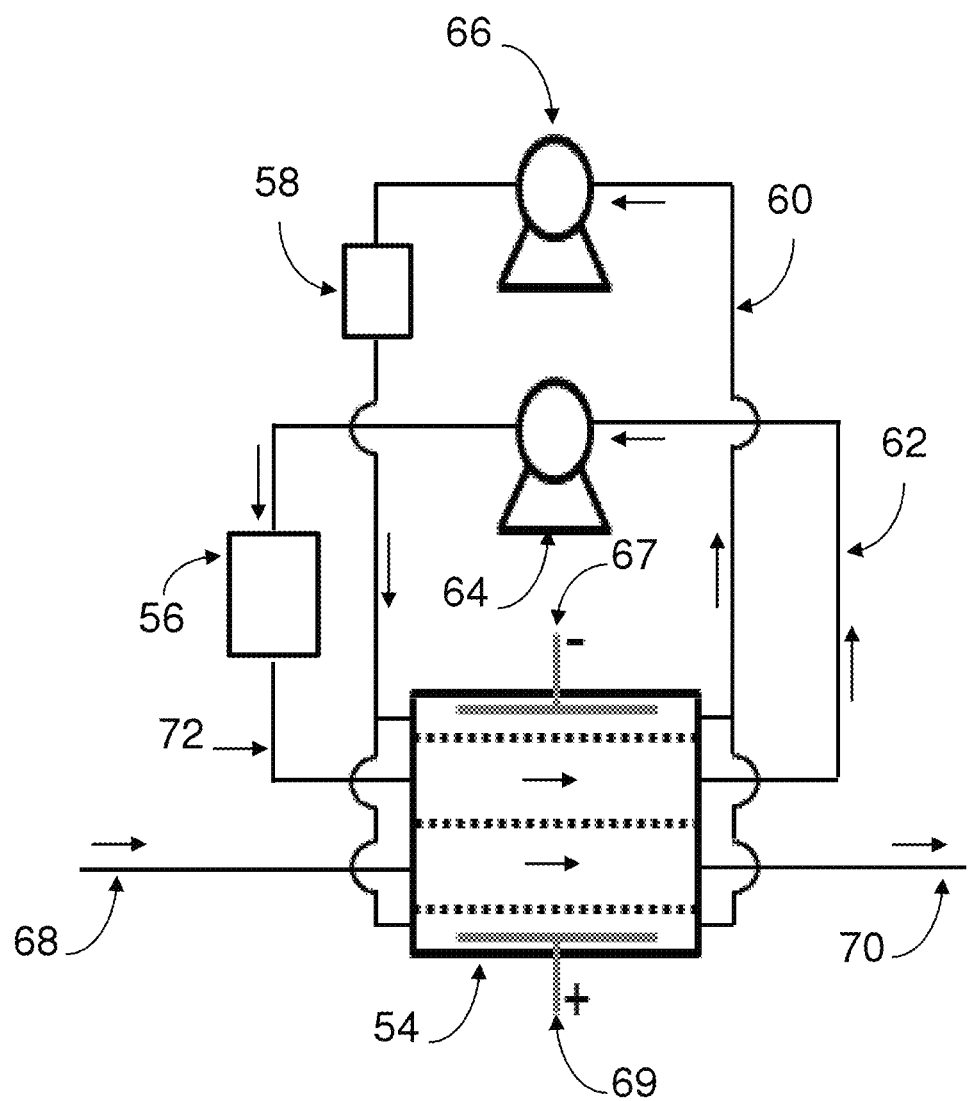
FIG. 6 is a flow diagram of a sodium management system consisting of an electrodialysis cell with concentrate and electrode rinse flow loops and dialysate or ultrafiltrate waste inlet and outlet diluate streams.

FIG. 6 shows a flow diagram for an electrodialysis system that can function as the sodium management system identified as 38 in FIGS. 1 and 2 and 52 in FIGS. 3, 4, and 5. The diluate inlet 68 to the electrodialysis system can be in fluid communication with dialysate from the flow loop 46 or with ultrafiltrate. The dialysate or ultrafiltrate enters the electrodialysis system at the diluate inlet 68 and passes through an electrodialysis cell 54. The electrodialysis cell 54 consists of a stack of alternating cation and anion exchange membranes.

In alternative embodiments, the electrodialysis cell 54 can contain a stack of bipolar and cation exchange membranes to result in alternating flow channels through the electrodialysis cell 54 (not shown). In particular, the bipolar membrane has an anion exchange membrane and a cation exchange membrane bonded together. Examples of bipolar membranes and cation exchange membranes that could be used include Neosepta BP-1E bipolar membrane and Neosepta CMX cation exchange membrane produced by ASTOM corporation. The cation exchange membrane is designed to only allow cations to pass through it. The bipolar membrane is designed to not allow cations and anions to pass through it. Upon entering the electrodialysis cell 54, the dialysate or ultrafiltrate passes through certain flow channels that are acidified during operation (not shown).

At each end of the membrane stack is an electrode 67 and 69 contained in an electrode compartment. The electrode compartment is continually rinsed during operation with an electrode rinse solution contained in the electrode rinse reservoir 58 and recirculated with the electrode rinse pump 66. The electrode rinse solution may consist of a potassium sulfate or sodium sulfate solution, or any other suitable electrode rinse solution. The use of sodium sulfate is preferred because oxidation of sulfate does not occur to an appreciable amount under normal typical operating conditions of 1 to 2 volts per cell pair. The use of sodium chloride in the electrode rinse must be avoided to prevent the oxidation of chloride to chlorine at the electrodes, which may diffuse into the diluate stream and contaminate the dialysate. The electrode rinse acts to continually flush reactants that may form at the electrode surfaces. For example, the electrolysis of water will occur to some extent at the electrodes resulting in the formation of hydrogen and oxygen. In some cases it will be desirable to include a degassing module in the electrode rinse circuit to remove some of the formed gases. The degassing module could consist of a hydrophobic membrane vent. The alternating stack of anion and cation exchange membranes results in alternating flow channels through the electrodialysis cell 54. The dialysate or ultrafiltrate waste passes through certain flow channels separated from another solution passing through the alternating flow channels. The solution referred to as concentrate is contained in the concentrate reservoir 56 and recirculated through the electrodialysis cell 54 with the concentrate pump 64. The concentrate solution may initially be water or a sodium chloride solution, or any other suitable solution. In certain embodiments, any potassium or magnesium electrolytes removed from an input solution to the electrodialysis cell 54 or any other sodium management system is not substantially reintroduced into the dialysate in the dialysate flow loop 46 or otherwise reintroduced to the blood via the dialyzer 20 or via any other means. In certain embodiments, only a physiologically-compatible dialysate is contacted with the dialyzer 20. A physiologically-compatible dialysate has a sodium chloride concentration from about 120 to about 150 mM NaCl with additional cations, such as $K^+$, $Ca^{2+}$ and $Mg^{2+}$, and buffer components.

During operation, the electrodialysis system illustrated in FIG. 6 works by passing the dialysate or ultrafiltrate solution into the electrodialysis cell 54 through the diluate inlet 68 while recirculating the electrode rinse 58 and concentrate 56 solutions. In order to achieve sodium removal from the dialysate or ultrafiltrate waste entering the electrodialysis cell 54, a voltage is applied across the electrodes 67 and 69 to promote movement of ions from the diluate stream to the concentrate stream. In one embodiment, in order to increase the sodium concentration of the dialysate or ultrafiltrate waste entering the electrodialysis cell 54, the voltage applied is reversed across the electrodes 67 and 69. Sodium is the major positive ion (cation) in the dialysate or ultrafiltrate solution having a concentration of about 135-155 mmol/L. Other positive cations such as magnesium, calcium and potassium are generally around 0.5, 1.5, and 5 mmol/L, respectively. Hence, sodium is the major transport ion in the electrodialysis system of FIG. 6.

Figure 7:
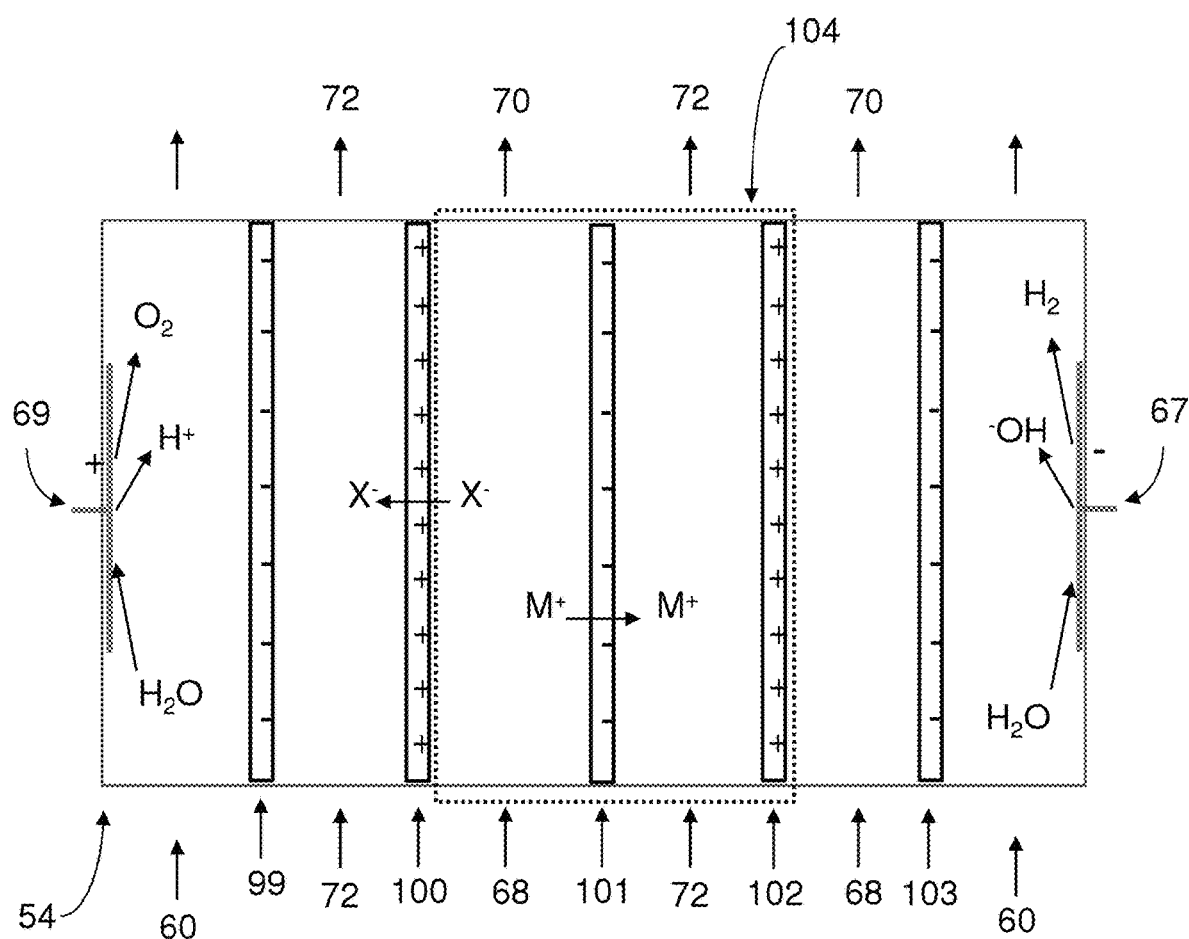
FIG. 7 is a flow diagram of an electrodialysis cell.

FIG. 7 shows a flow diagram detailing the electrodialysis cell 54. A diluate stream 68 enters the electrodialysis cell 54 between a cation exchange membrane 101 and an anion exchange membrane 100. With a potential applied across the electrodes anions (X−) are drawn towards the anode 69 and flow through the anion exchange membrane 100. Cations (M+) are drawn towards the cathode 67 and flow through the cation exchange membrane 101. The anions and cations are collected in separate flow streams known as concentrate streams 72. The dashed line in FIG. 7 highlights a single stack, or cell 104 contained in the electrodialysis cell 54. Multiple cells can be stacked together in the configuration shown of alternating cation and anion exchange membranes. Multiple cells will result in multiple diluate 68 and concentrate 72 streams entering the electrodialysis cell 54, which are recombined upon exiting the electrodialysis cell 54. Also, shown in FIG. 7 are the electrode rinse streams 60 flowing past the anode 69 and cathode 67. A common electrode reaction that results is the electrolysis of water with the side products illustrated. The electrode rinse acts to sweep these side products away from the electrodes in order to maximize current efficiency in the electrodialysis cell 54. The electrode rinse streams 60 from the anode 69 and cathode 67 are preferably combined, as illustrated in FIG. 6, in order to neutralize any hydrogen and hydroxyl ions formed. Finally, the placement of cation exchange membranes 99 and 103 next to the electrodes prevents the transport of chloride into the anode 69 compartment. Chloride is easily oxidized to chlorine at the anode and if formed could cause harm to the patient. The cation and anion exchange membranes could include any commercially available cation and anion exchange membranes, such as Neosepta CMX and Neosepta AMX, respectively, produced by ASTOM Corporation (Japan). The electrodes could be made from any suitable material including platinum, carbon, titanium, steel, or other materials known to those skilled in the art.

Figure 8:
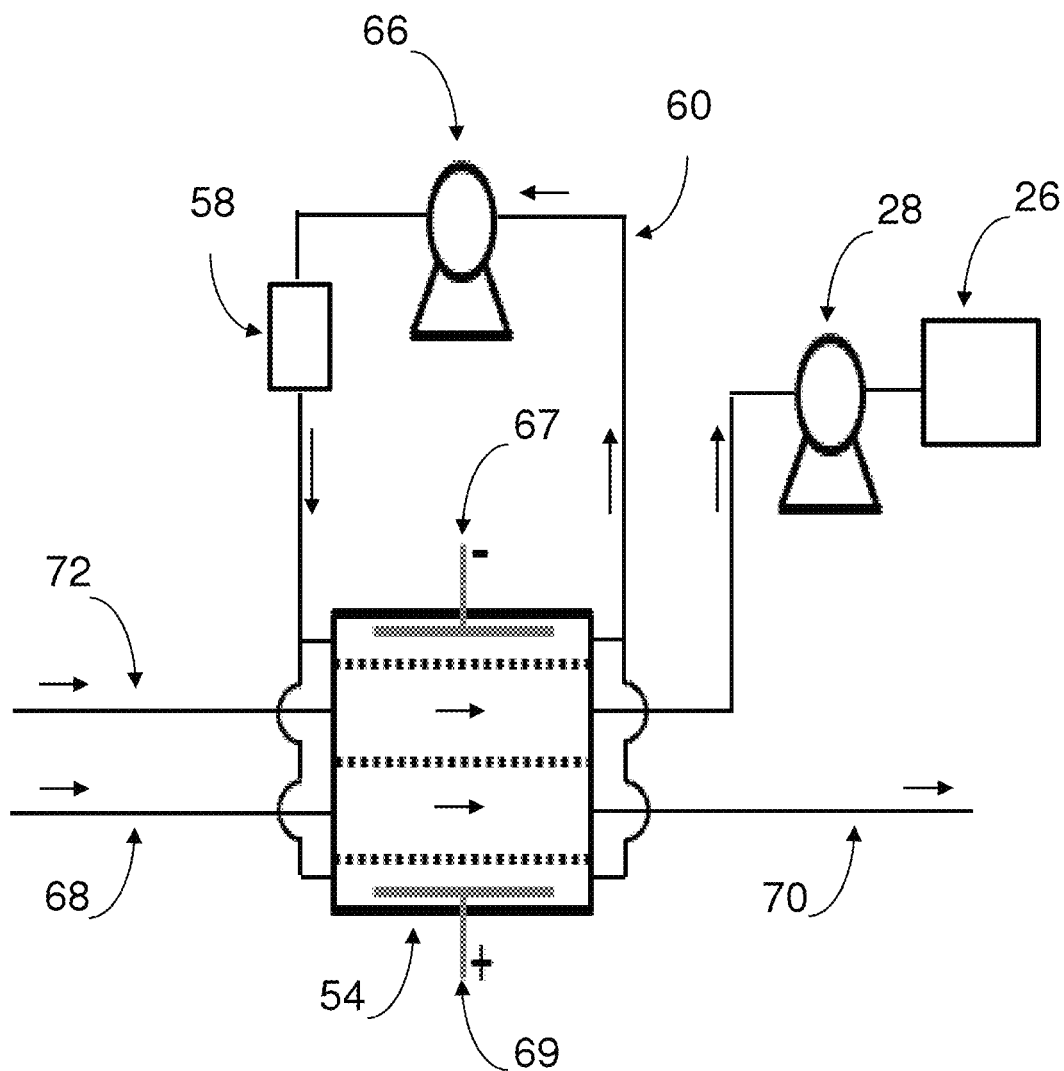
FIG. 8 is a flow diagram of a sodium management system having an electrodialysis cell with an electrode rinse flow loop, dialysate inlet and outlet diluate streams and ultrafiltrate waste inlet and outlet concentrate streams.

FIG. 8 shows a flow diagram for an electrodialysis system that can be utilized in FIGS. 1 and 2 as a sodium management system 38 or as sodium management system 52. The operation is the same as that described for the system shown in FIG. 6, except the ultrafiltrate from the ultrafiltration reservoir 52 or dialysate from the dialysate reservoir 48 is utilized as the concentrate solution. As shown in FIG. 8, the concentrate solution 72 passes through the electrodialysis cell 54 by being drawn with the ultrafiltration pump 28 and collected in the ultrafiltration reservoir 26. Utilization of the ultrafiltrate or dialysate from the dialysate reservoir 48 minimizes the amount of fluid necessary to operate the system.

Figure 9:
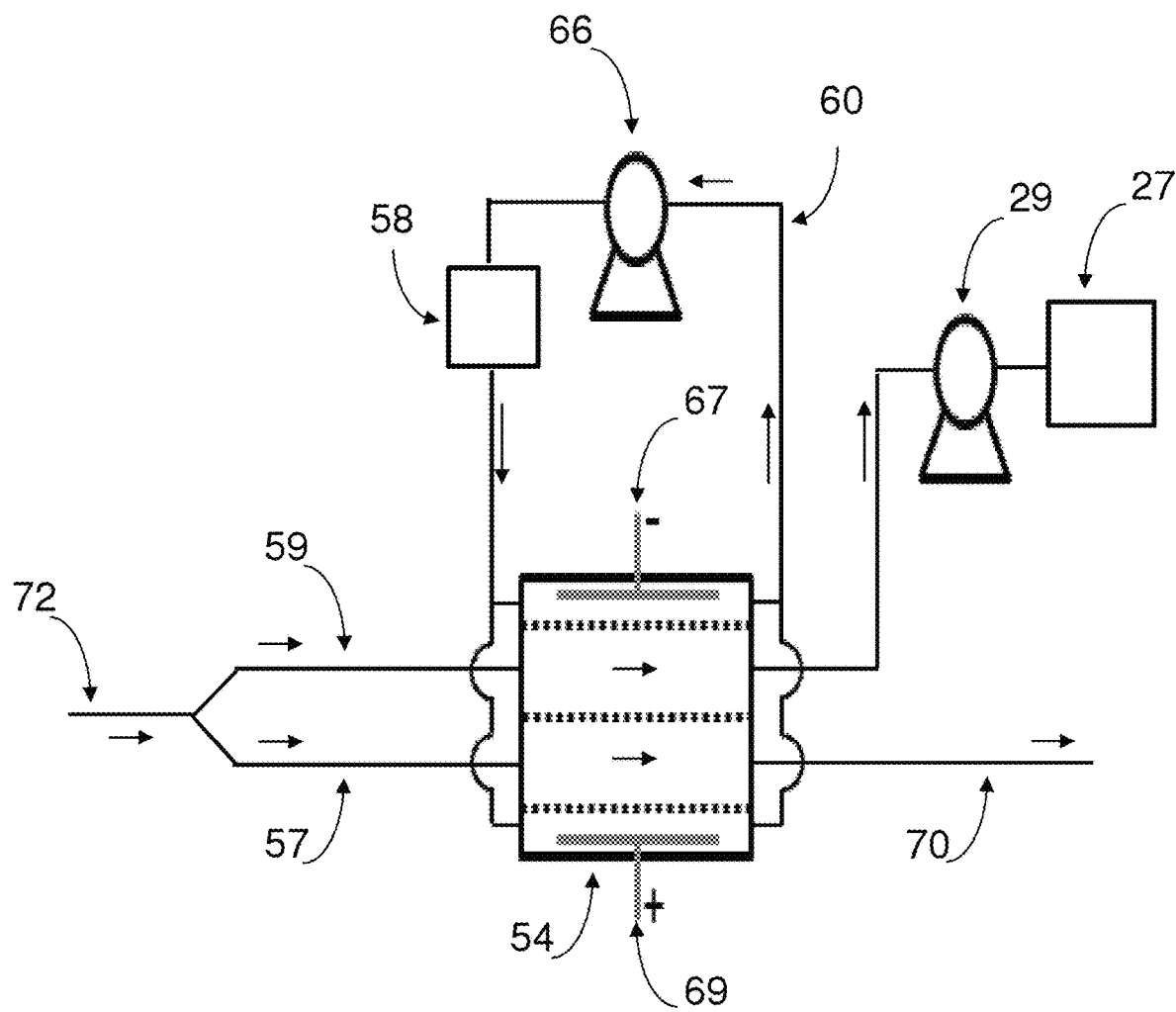
FIG. 9 is a flow diagram of a sodium management system having an electrodialysis cell with an electrode rinse flow loop, split ultrafiltrate waste streams to generate inlet and outlet diluate and concentrate streams.

FIG. 9 shows a flow diagram for an electrodialysis system that can function as the sodium management system identified as 52 in FIGS. 3, 4, and 5 or as sodium management system 38. The operation is the same as that described for the system shown in FIG. 8, except the diluate stream 57 and concentrate stream 59 are generated from the ultrafiltrate stream 72. The ultrafiltrate stream 72 is split into two streams, a diluate inlet 57 and a concentrate inlet 59. The amount of flow split between the streams is determined by the ultrafiltrate concentrate pump 29. The ultrafiltrate concentrate fluid is collected in an ultrafiltrate concentrate reservoir 27. Utilization of the ultrafiltration stream minimizes the amount of fluid necessary to operate the system.

The electrodialysis systems described above can be used for several months of operation. The main replaceable components of electrodialysis systems are the ion-exchange membranes. Over time the membranes may get fouled or lose their selectivity and require replacement. One method to increase the lifetime of the membranes is to run a cleaning solution through the electrodialysis system after a dialysis run. The cleaning solution could consist of a citric acid solution. The cleaning solution may also serve the function of disinfecting the dialysis system flow loop for reuse.

Another feature of the electrodialysis system is the generation of a concentrate solution. If the electrodialysis system is placed after the dialysate regeneration system then the concentrate solution will consist mainly of sodium chloride. This concentrated sodium chloride solution could potentially be used to regenerate any cation-exchange resins contained in the dialysate regeneration unit 32. For example, passing the concentrated sodium chloride solution through the zirconium phosphate loaded with ammonium, calcium, magnesium and potassium, after a dialysis run, will remove the waste cations and replace them with sodium. The zirconium phosphate can then be reused for the next run.

Figure 10:
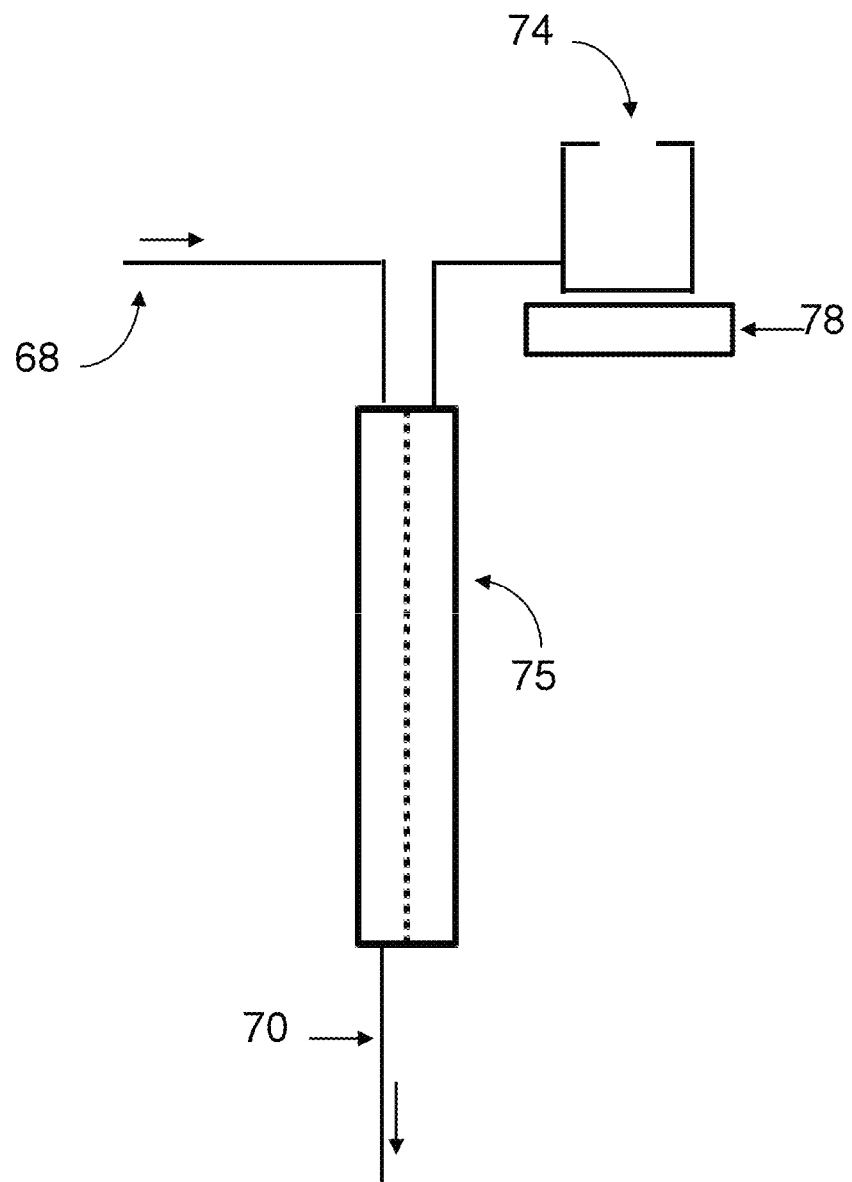
FIG. 10 is a flow diagram of a sodium management system having a reverse osmosis membrane module, a fluid reservoir positioned on a load cell and dialysate inlet and outlet streams.

FIG. 10 shows a flow diagram for a forward osmosis system that can function as the sodium management system identified as 38 in FIGS. 1 and 2. The dialysate inlet stream 68 passes through a reverse osmosis module 75. The reverse osmosis module consists of one or several osmotic membranes separated into two chambers. The reverse osmosis module can be in a spiral wound configuration, a plate-and-frame format, or hollow fibers. The dialysate inlet stream 68 enters on one side of the reverse osmosis module 75 and a low osmotic fluid, such as water, is contained in a water reservoir 74 on the other side of the module. As dialysate fluid passes through the module 75, fluid from the water reservoir 74 will transfer into the dialysate fluid because of their osmotic pressure difference. The fluid from the water reservoir 74 will act to dilute the sodium concentration of the dialysate. For operation in the controlled compliant dialysate system shown in FIG. 1, a water reservoir load cell 78 is necessary. The load cell 78 will determine how much fluid is being transferred to the dialysate and can be used to adjust the ultrafiltrate waste pump 28 to maintain fluid balance. Otherwise the additional fluid would be added back to the patient, or increase the pressure to unacceptable levels in the dialysate circuit. For the case of the dialysate system shown in FIG. 2, with an open, non-fixed volume dialysate loop the water reservoir load cell 78 is not necessary, the extra volume added from the water reservoir 74 will simply fill the dialysate reservoir 48. While the system of FIG. 10 is by-passed with the by-pass flow loop 36, the pressure at the dialysate inlet 68 and outlet 70 will slowly increase until reaching the osmotic pressure of the dialysate, which could be as high as 200 psi. The tubing and components of FIG. 10 must be selected to withstand a pressure of 200 psi.

Figure 11:
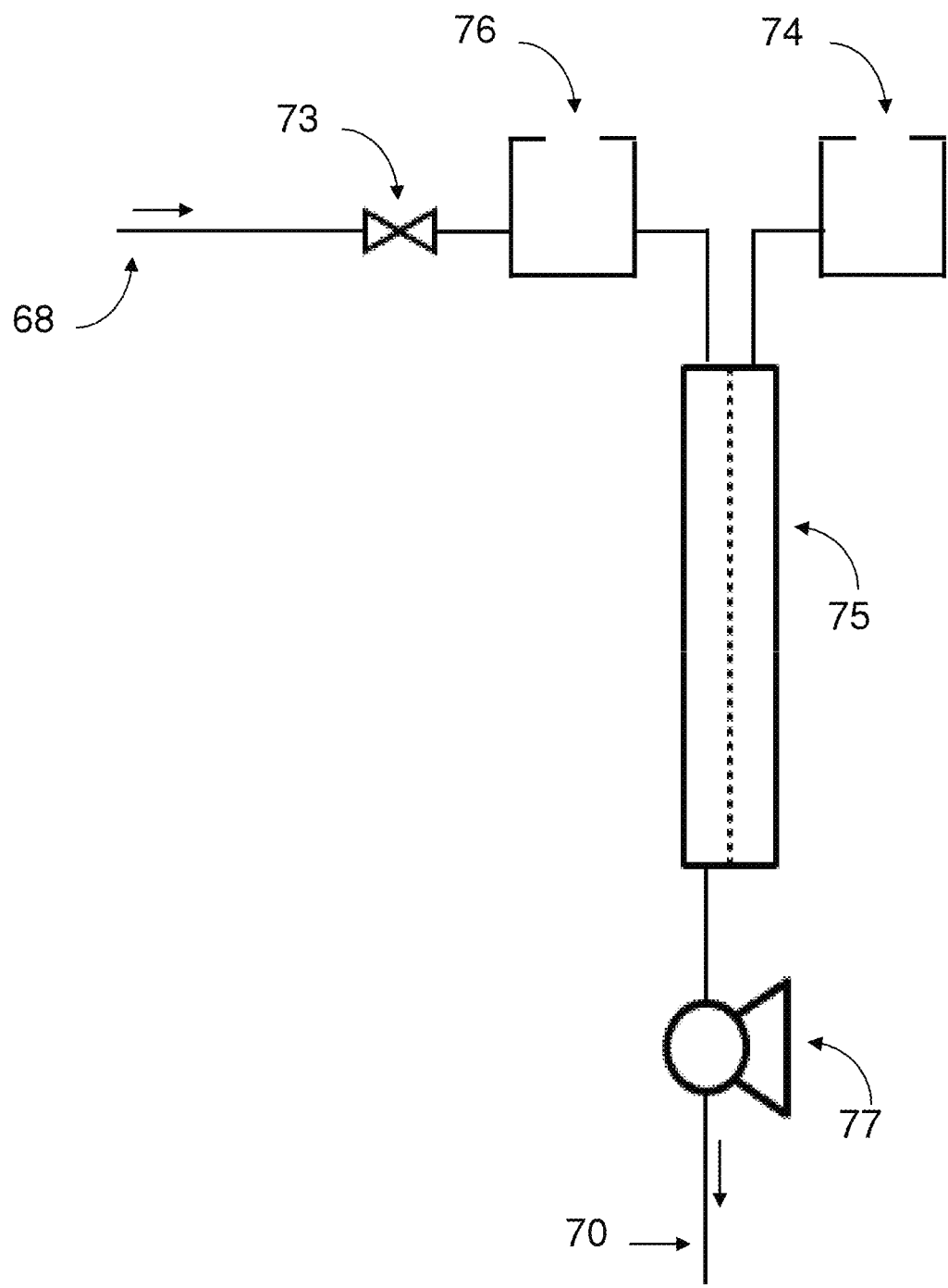
FIG. 11 is a flow diagram of a sodium management system having a reverse osmosis membrane module, a fluid reservoir, a dialysate reservoir, a metering pump and inlet and outlet dialysate streams.

FIG. 11 shows a flow diagram for a forward osmosis system that can function as the sodium management system identified as 38 in FIGS. 1 and 2. The dialysate inlet stream 68 passes through a reverse osmosis module 75. The reverse osmosis module consists of one or several osmotic membranes separated into two chambers. The reverse osmosis module may be in a spiral wound configuration, a plate-and-frame format, or hollow fibers. The dialysate inlet stream 68 enters a reservoir 76 on one side of the reverse osmosis module 75 and a low osmotic fluid, such as water, is contained in a water reservoir 74 on the other side of the module. As dialysate fluid passes through the module 75 fluid from the water reservoir 74 will transfer into the dialysate fluid because of their osmotic pressure difference. The fluid from the water reservoir 74 will act to dilute the sodium concentration of the dialysate. Flow regulator 73 and a metering pump 77 determine the amount of flow passing through the system of FIG. 11. During initial operation, dialysate fluid enters the forward osmosis system and fills reservoir 76 to a certain level by having restricted flow through the metering pump. The metering pump 77 is then set to a flow rate based on the sodium adjustment necessary and the ultrafiltrate waste pump 28 is adjusted to maintain fluid balance within the dialysate loop 46. Water from the reservoir 74 will flow across the osmotic membrane. If the flow rate of water across the membrane is greater than the flow rate of the metering pump 77 reservoir 76 will increase in volume. Reservoir 76 is designed to allow various volumes by venting to the atmosphere or by being made out of a compliant material that can change in volume.

Figure 12:
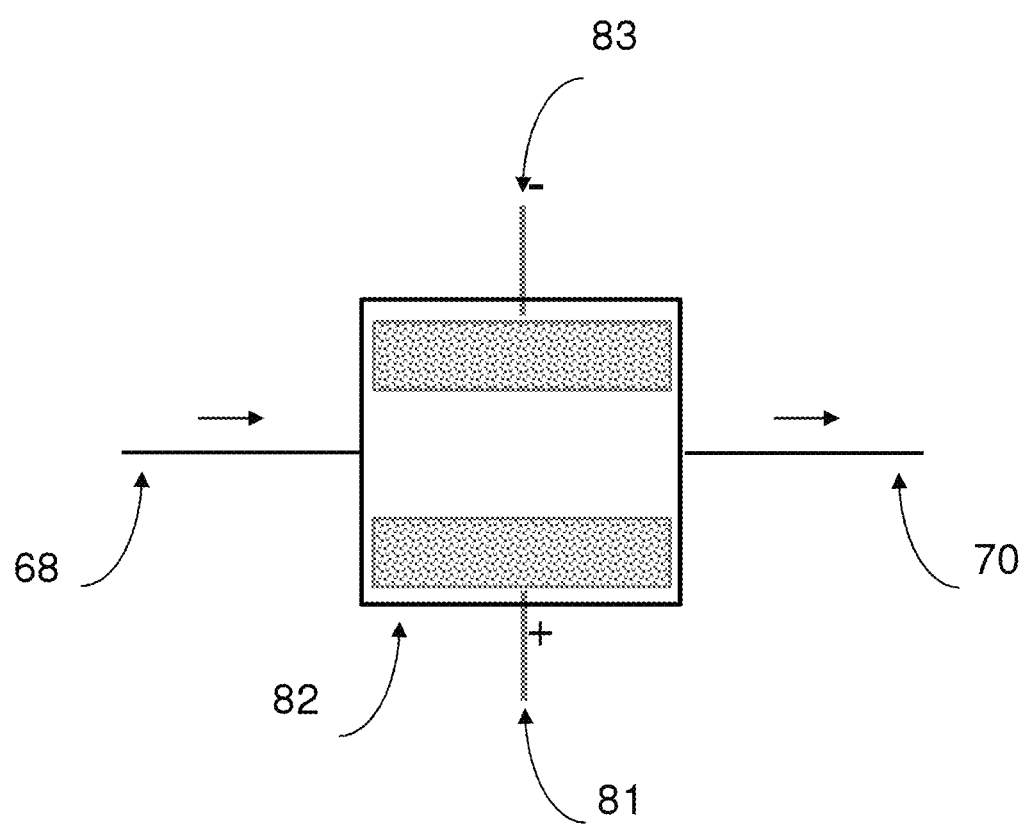
FIG. 12 is a flow diagram of a sodium management system having a capacitive deionization unit and dialysate or ultrafiltrate waste inlet and outlet streams.

FIG. 12 shows a flow diagram for a capacitive deionization system that can function as the sodium management system identified as 38 in FIGS. 1 and 2 and 52 in FIGS. 3, 4, and 5. The diluate inlet 68 to the capacitive deionization system may consist of dialysate or ultrafiltrate waste. The dialysate or ultrafiltrate waste enters the capacitive deionization system at the diluate inlet 68 and passes through a capacitive deionization cell 82. The capacitive deionization cell 82 consists of at least two electrodes 81 and 83 at each end. The electrodes may consist of carbon or other suitable material. When a voltage is applied across the electrodes, ions in the dialysate or ultrafiltrate waste will be drawn to the electrodes, resulting in an outlet stream 70 that will have a lower concentration of ions, namely sodium and its counter ions. Non-ionic species such as urea will not be affected by the capacitive deionization system. The capacitive deionization cell may contain several electrode pairs stacked in parallel to increase the total electrode surface area and ultimately the capacity to remove sodium ions from the dialysate or ultrafiltrate waste streams. The capacitive deionization system may also be used to increase the sodium concentration of the dialysate by reversing the polarity of the electrodes for a period of time or reducing the voltage across the electrodes to zero for a period of time. This will act to force sodium ions off of the electrodes into the dialysate or ultrafiltrate stream.

Figure 13:
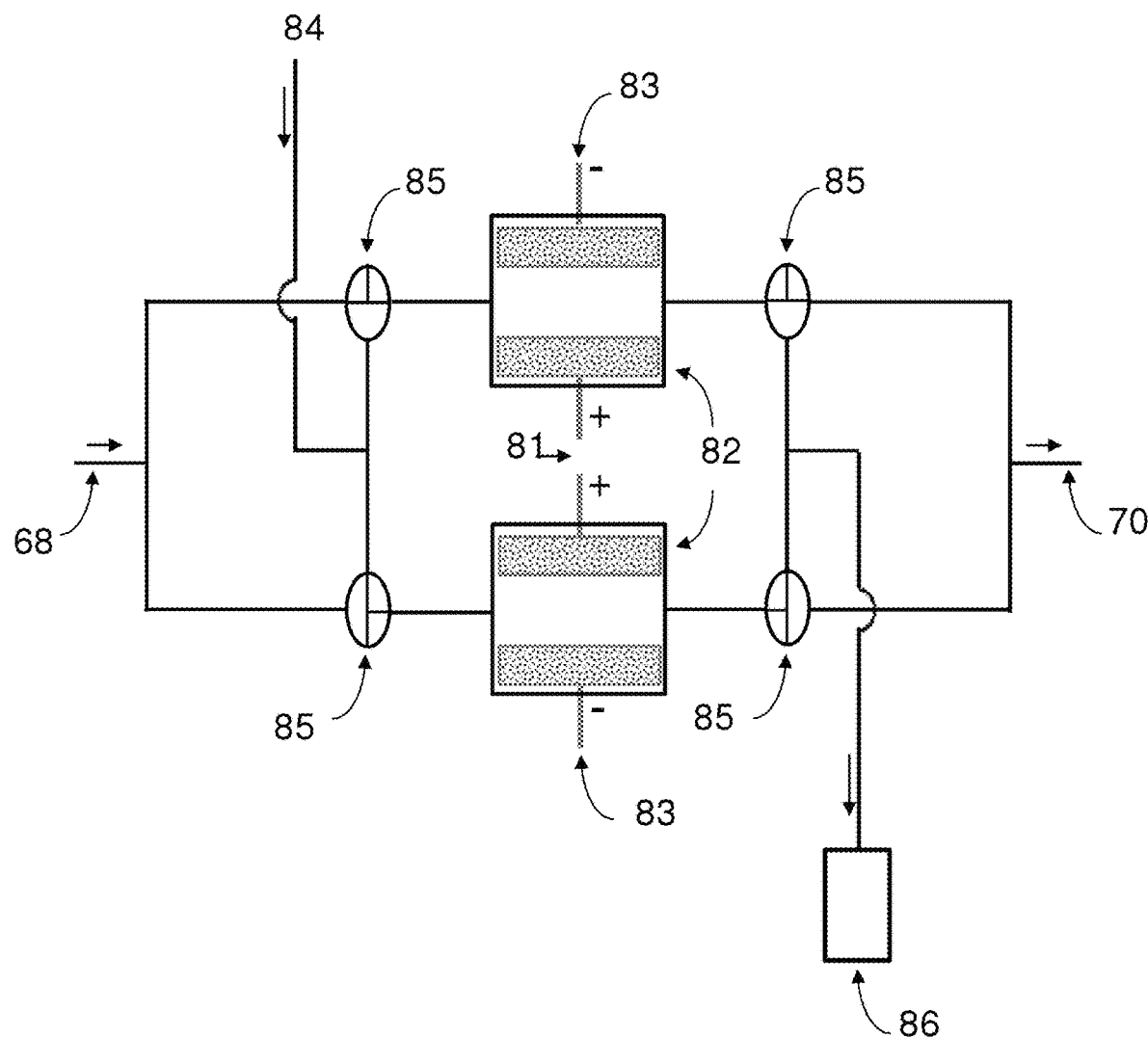
FIG. 13 is a flow diagram of a sodium management system having two capacitive deionization units, a flow path for a flushing fluid and dialysate or ultrafiltrate waste inlet and outlet streams.

FIG. 13 also shows a flow diagram for a capacitive deionization system that can function as the sodium management system identified as 38 in FIGS. 1 and 2 and 52 in FIGS. 3, 4, and 5. The diluate inlet 68 to the capacitive deionization system may consist of dialysate or ultrafiltrate waste. The dialysate or ultrafiltrate waste enters the capacitive deionization system at the diluate inlet 68 and passes through one of two capacitive deionization cells 82. The capacitive deionization cells 82 have at least two electrodes 83 and 84 at each end. The electrodes may consist of carbon or other suitable material. When a voltage is applied across the electrodes, ions in the dialysate or ultrafiltrate waste will be drawn to the electrodes, resulting in an outlet stream 70 that will have a lower concentration of ions, namely sodium and its counter ions. The capacitive deionization cells can contain several electrode pairs stacked in parallel to increase the total electrode surface area and ultimately the capacity to remove sodium ions from the dialysate or ultrafiltrate waste streams. The presence of two capacitive deionization cells allows one cell to be regenerated while the other cell is removing sodium. A flushing flow stream 84 can enter either cell depending on the placement of four three-way valves 85. Other placement options for the three-way valves 85 to accomplish the same flow control function are possible and are within those of skill in the art. The valves also determine which capacitive deionization cell the dialysate or ultrafiltrate waste enters. FIG. 13 shows the appropriate valve positions for the flushing fluid 84 to pass through the bottom cell and the dialysate or ultrafiltrate waste fluid 68 to pass through the top cell. The flushing fluid may consist of ultrafiltrate waste, water from an additional reservoir, or a cleaning solution such as sodium citrate. The capacitive deionization cell can be regenerated using a flushing fluid by temporarily reversing the polarity of the electrodes to force the ions off, and then by reducing the voltage across the electrodes to zero to prevent re-binding of ions in the flushing solution. After passing through the cell, the flushing solution is collected in a reservoir 86. The method of using two capacitive deionization cells allows for continual regeneration during a hemodialysis run, which will minimize the surface area requirements of the electrodes and reduce the overall system size. The capacitive deionization system may also be used to increase the sodium concentration of the dialysate by reversing the polarity of the electrodes for a period of time or reducing the voltage across the electrodes to zero for a period of time. This will act to force sodium ions off of the electrodes into the dialysate or ultrafiltrate stream. The single unit capacitive deionization system shown in FIG. 12 could also operate in a flushing mode for regeneration of the electrodes. For example, if a three-way valve is placed along the outlet steam 70 with an additional flow path to a waste reservoir, periodically the dialysate could be diverted to the waste reservoir to flush the electrodes. The method of reversing the polarity during the flushing process would maximize the regeneration of the electrodes and minimize the amount of dialysate fluid required.

Figure 14:
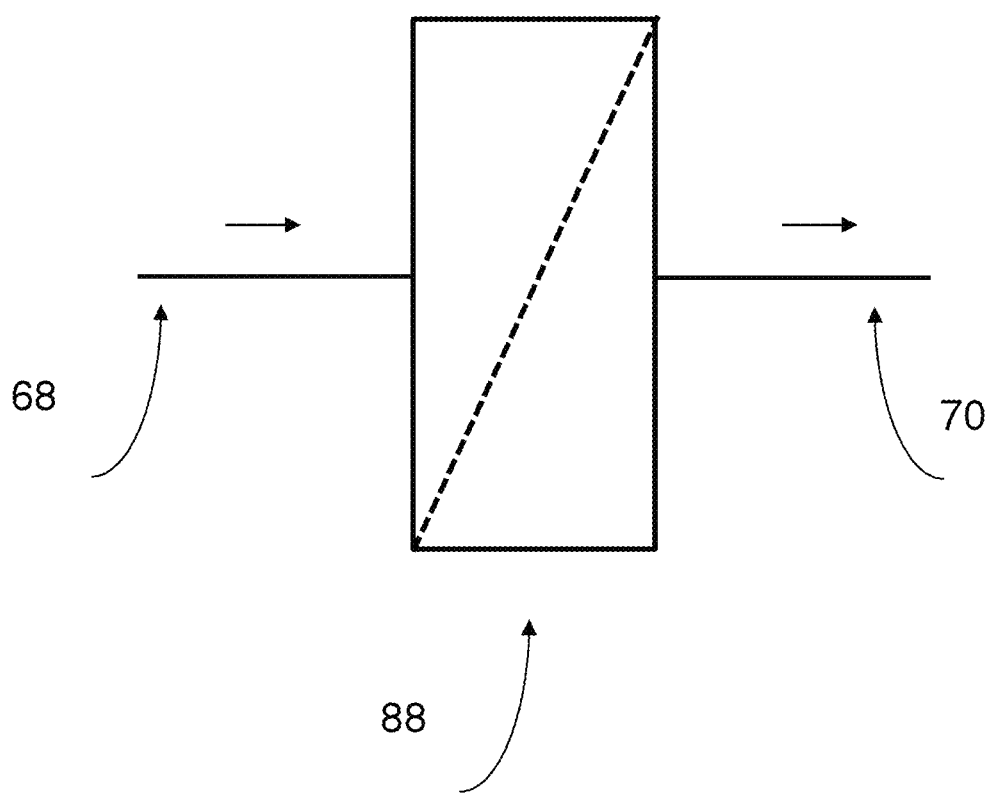
FIG. 14 is a flow diagram of a sodium management system having a reverse osmosis module and ultrafiltrate waste or dialysate inlet and outlet streams.

FIG. 14 shows a flow diagram for a reverse osmosis system that can function as the sodium management system 38 as in FIGS. 1 and 2 and identified as 52 as in FIGS. 3, 4, and 5. The ultrafiltrate waste or dialysate stream 68 enters a reverse osmosis module 88 and a fluid substantially free from ionic species exits from the module through the outlet 70. The reverse osmosis module is as described for FIGS. 10 and 11. Preferably, the membrane in the reverse osmosis module 88 will have a high sodium rejection fraction, greater than 95%. Therefore, if the ultrafiltrate waste or dialysate inlet stream 68 entering the module has a concentration of 100 mM sodium the outlet stream 70 will only have a concentration of 5 mM or lower. The membrane surface area of the reverse osmosis module must also be sized appropriately to prevent excessive pressure requirements for the fluid to pass through the membrane.

EXAMPLE

Electrodialysis for Sodium Management

A lab-scale electrodialysis experiment was performed to determine the requirements to remove sodium generated from an ion-exchange based dialysate regeneration system. Assuming a 5 day/week hemodialysis schedule with a 70-kg patient generating BUN at a rate of 63 grams/week. The amount of urea to be removed from the dialysate per session will be 470 millimoles. Also, assuming a sorbent system similar to the REDY is utilized for dialysate regeneration. The 470 millimoles of urea will generate 940 millimoles of ammonium which will displace up to 940 millimoles of sodium ion during the ion-exchange reaction in the zirconium phosphate layer. Also, assuming a session time of 3 hours, the average rate of sodium generation will be 5 millimoles per minute. Therefore, it is desirable to have an electrodialysis system that can remove sodium at a rate of 5 millimoles per minute to maintain a constant dialysate sodium concentration.

To perform laboratory experiments an electrodialysis module, model ED64004, was purchased from PCCell (Germany). The unit consists of 10 cell pairs with 11 Neosepta CMX cation exchange membranes and 9 Neosepta AMX anion exchange membranes, purchased from ASTOM Corporation (Japan). Each membrane has an active area of 64 $cm^2$ resulting in a total active area of 1280 $cm^2$. The electrodes are titanium with a platinum/iridium coating.

The module was set-up similar to FIG. 6, with a 1 liter concentrate reservoir 56 initially filled with deionized water. The electrode rinse reservoir 58 was filled with 250 ml of 100 mM sodium sulfate. The concentrate and electrode rinse circuits were recirculated with peristaltic pumps. Also, the diluate feed solution was fed into the cell 68 with a peristaltic pump. One experiment utilized 140 mM sodium chloride as the feed solution with a flow rate of 80 ml/min. The concentrate and electrode rinse flow loops were recirculated at 100 ml/min. An 8 volt DC potential was applied to the electrodialysis module. After twenty-five minutes a sample was pulled from the outlet of the diluate stream and analyzed for sodium concentration using a CCX analyzer manufactured by NovaBiomedical. Also, the current was monitored using a Fluke 179 True RMS multimeter. The results showed a sodium drop from 140 to 99 mM at a flow rate of 80 ml/min with a current of 590 milliamps. Equivalent to a 3.3 millimole per minute sodium removal rate, or 26 millimole per minute per meter-squared. Therefore, to achieve a 5 millimole per minute sodium removal a surface area of 1920 $cm^2$ is required, or an additional 5 membrane pairs for the system used. The approximate size of an electrodialysis unit suitable for a 5 millimole per minute sodium removal rate would be 8 cm thick and 10 cm wide by 10 cm tall, or 800 ml in volume. The total weight filled with fluid would be approximately 2 kilograms. In the example given only 1.25 liters of water would be necessary to manage the sodium generation with the electrodialysis system. For comparison, if fresh water was used to dilute the dialysate sodium, approximately 6 liters of water would be necessary to manage a sodium generation rate of 5 millimoles per minute for 3 hours.

Hemofiltration, Hemodiafiltration and Peritoneal Dialysis Applications

FIG. 15 shows a flow diagram for a hemofiltration system utilizing a filtrate regeneration unit 33 and a sodium management system 38. The blood enters via line 22 to a hemofilter 101 and a portion is filtered across membranes contained in the hemofilter 101. The hemofilter 101 can consist of a hollow-fiber dialyzer, plate-and-frame dialyzer, or other suitable hemofilters. The hemofilter 101 can contain high flux or low flux membranes made from polysulfone, polyethersulfone, poly(methyl methacrylate), cellulose, modified-cellulose or other suitable materials. The filtration pump 105 determines the amount of filtrate coming across the hemofilter. The filtrate 103 exiting the hemofilter 101 flows past an ultrafiltration pump 28 whereby ultrafiltrate is removed from the filtrate and collected in an ultrafiltration reservoir 26. The filtrate then passes through a filtrate regeneration unit 33, sodium management system 38, and infusate system 43 as described above. The regenerated filtrate 109 then passes through a microbial filter 111 before being directly infused into the blood as replacement fluid. The microbial filter 111 could include an ultrafilter filter, sterile filter, or other suitable microbial filters. The microbial filter 111 can contain membranes made from the same materials suitable for the hemofilter, preferably with pore sizes 0.2 microns or smaller. The microbial filter 111 may remove both viable organisms and endotoxin. The microbial filter may be a single filter, or multiple filters, including redundant filters. The hemofiltration system shown in FIG. 15 has a controlled compliant system, with filtrate flow loop 107. In certain embodiments, the flow loop 107 can be non-compliant or non-expandable. Hemofiltration has certain benefits over hemodialysis including higher convective clearance which increases the clearance rate of middle molecular weight species like beta-2-microglobulin.

Figure 16:
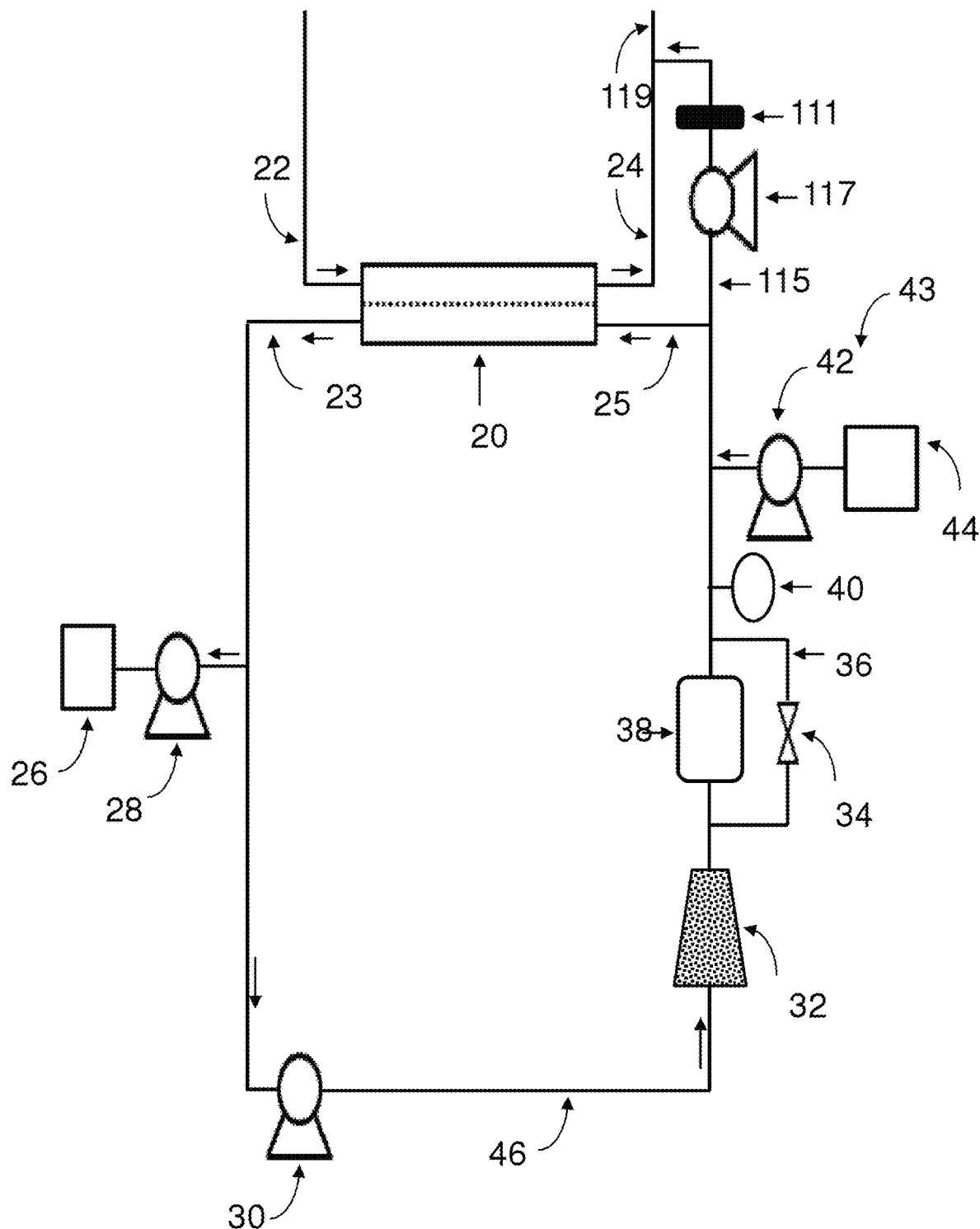
FIG. 16 is a flow diagram of a hemodiafiltration regeneration system with a controlled compliant diafiltration circuit and a sodium management system.

FIG. 16 shows a flow diagram for a hemodiafiltration system utilizing a dialysate regeneration unit 32 and a sodium management system 38. The blood enters via line 22 to a dialyzer 20 and a portion is filtered across membranes contained in the dialyzer 20. The dialyzer 20 can consist of a hollow-fiber dialyzer, plate-and-frame dialyzer, or other types of dialyzers. The dialyzer 20 can contain high flux or low flux membranes made from polysulfone, polyethersulfone, poly(methyl methacrylate), cellulose, modified-cellulose or other suitable materials. The dialysate 23 exiting the dialyzer 20 flows past an ultrafiltration pump 28 whereby a volume of fluid is removed from the dialysate and collected in an ultrafiltration reservoir 26. The dialysate is recirculated in the dialysate flow loop 46 with a dialysate pump 30. The dialysate then passes through a dialysate regeneration unit 32, sodium management system 38, and infusate system 43 as described above. A portion of the regenerated dialysate 115 is removed from the dialysate flow loop 46 with the replacement fluid pump 117 and passed through a microbial filter 111 and then directly infused into the blood as replacement fluid. The microbial filter 111 can include an ultrafilter filter, sterile filter, or other suitable microbial filters. The microbial filter 111 can contain membranes made from the same materials suitable for the dialyzer, preferably with pore sizes 0.2 microns or smaller. The microbial filter 111 may remove both viable organisms and endotoxin. The microbial filter may be a single filter, or multiple filters, including redundant filters. The hemodiafiltration system shown in FIG. 16 has a controlled compliant dialysate system, with flow loop 46. In certain embodiments, the flow loop 46 can be non-compliant or have a non-expandable volume. Hemodiafiltration combines the benefits achieved with hemodialysis and hemofiltration, including maximum small molecule diffusive clearance and maximum middle molecule convective clearance.

Figure 17:
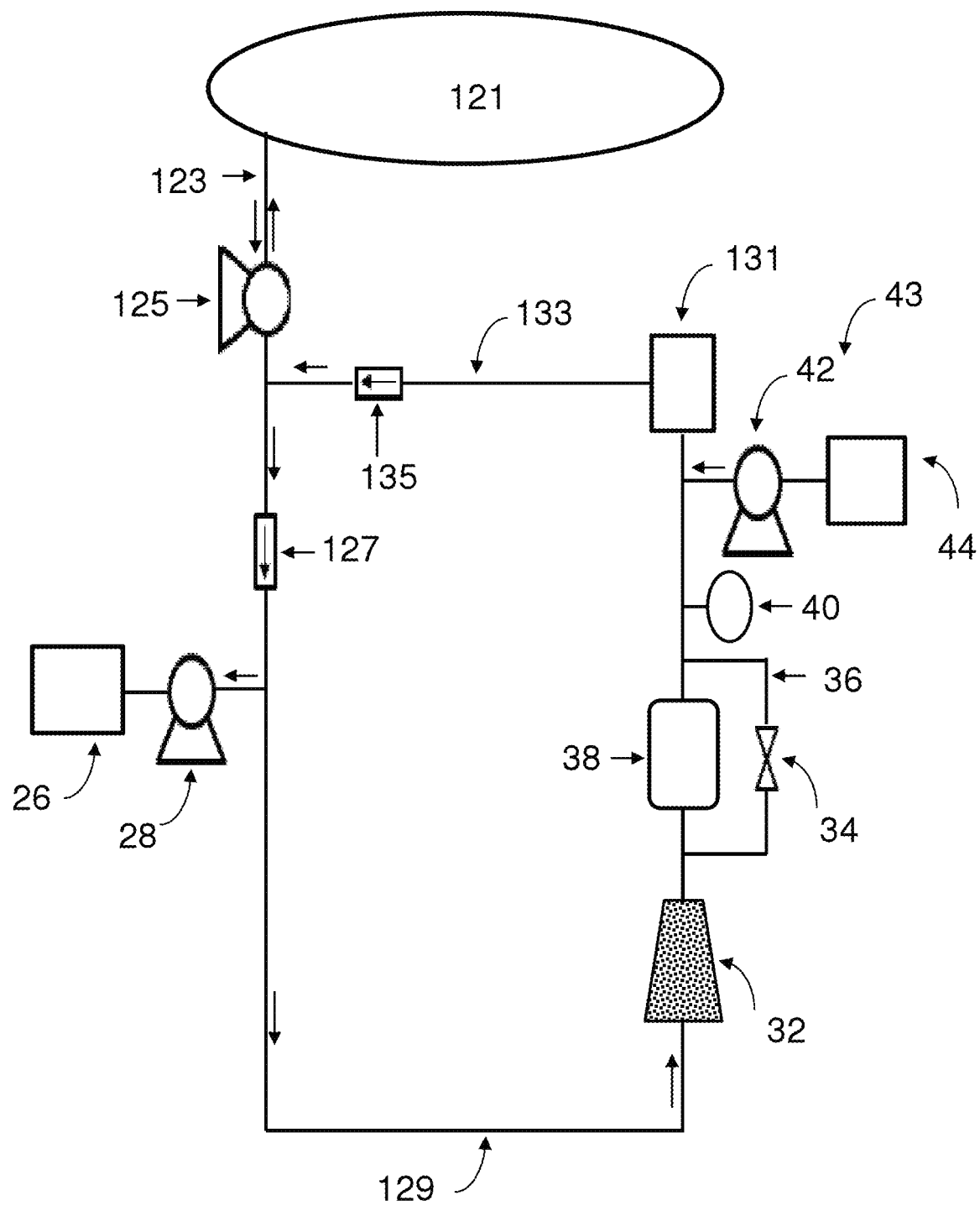
FIG. 17 is a flow diagram of a peritoneal dialysate regeneration system and a sodium management system.

FIG. 17 shows a flow diagram for a peritoneal dialysis system utilizing a dialysate regeneration unit 32 and a sodium management system 38. Initially, a patient's peritoneal cavity 121 is filled with a certain volume of dialysate. After a certain period of time, spent dialysate is drawn out of the peritoneal cavity 121 through a catheter 123 with a reversible dialysate pump 125. The spent dialysate flows through a check valve 127 and is prevented from flowing through flow line 133 because of a check valve 135. The spent dialysate continues through the dialysate regeneration unit 32 via flowpath 129 to sodium management system 38 and the infusate system 43. In the case of peritoneal dialysis, the infusate system 43 can include infusate containing high levels of glucose or icodextrin in certain embodiments. The regenerated dialysate is collected in a dialysate reservoir 131. After a desired amount of regenerated dialysate has been collected in the dialysate reservoir 131 the dialysate pump 125 is reversed and fluid is drawn out of the dialysate reservoir 131. The fluid flows through a check valve 135 and is directed through the catheter 123 back into the peritoneal cavity. Those skilled in the art will recognize that other configurations of pumps and valves can accomplish the same function, for example, valves 127 and 135 can be combined into a single 3-way valve, or pump 125 may be non-reversible if valves 127 and 135 are 2-way valves and pump 125 is placed downstream from valve 127. This process can be continued until the dialysate regeneration system is exhausted or until the therapy is complete. At the end of a therapy, the patient will have collected a certain volume of ultrafiltrate in their peritoneal cavity. The ultrafiltrate can be removed using the ultrafiltration pump 28 and collected in the ultrafiltration reservoir 26. Likewise, during the therapy, while spent dialysate is being removed from the patient, a portion of the spent dialysate can be removed as ultrafiltrate with the ultrafiltrate pump 28. However, the amount of ultrafiltrate a patient generates is variable and depends on several factors including properties of their peritoneum, dialysate composition, and patient fluid volume, or overload. Therefore, care must be taken when operating the ultrafiltrate pump 28 during the therapy in order to avoid depleting the dialysate contained in the peritoneal cavity 121.

It will be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

What is claimed is:

1. A system, comprising:
a dialysate flow loop for circulating a dialysate through a dialyzer where at least one waste species enters the dialysate;
a dialysate regeneration unit comprising a sorbent cartridge having activated carbon, a single inlet, and a single outlet positioned in the dialysate flow loop for removing at least a portion of the at least one waste species and releasing at least a first conductive species to the dialysate or absorbing at least a second conductive species from the dialysate;
a conductivity detector that measures the conductivity or sodium ion concentration of the dialysate;
a sodium management system for generating a sodium-modified fluid for controlled addition to the dialysate in the dialysate flow loop, the sodium-modified fluid generated by the sodium management system from any one of an input dialysate, input ultrafiltrate, input solid sodium salt or input concentrated sodium resulting in a sodium ion concentration or conductivity that is higher or lower than the dialysate in the dialysate flow loop;
wherein the sodium management system is positioned on a bypass conduit; the bypass conduit having an inlet and an outlet fluidly connected to the dialysate flow loop between the single inlet of the dialysate regeneration unit and an outlet of the dialyzer, bypassing at least a portion of the dialysate flow loop, wherein the sodium management system removes sodium ions from the dialysate, stores the sodium ions removed from the dialysate, and selectively releases the sodium ions removed from the dialysate between the single inlet of the dialysate regeneration unit and the outlet of the dialyzer to increase the sodium ion concentration of the dialysate through modulation of an electrical field using an electrode polarity of the sodium management system such that no additional sodium ions are added to the dialysate after the sodium management system and prior to the dialyzer, wherein concentrations of non-sodium positive ions in the dialysate are increased through introduction of solutions prepared by a reconstitution system outside of the sodium management system,
wherein the bypass conduit includes a pump and defines a flow path through a first conduit fluidly connecting the dialysate flow loop to a reservoir, a second conduit fluidly connecting the reservoir to the sodium management system, and a third conduit fluidly connecting the sodium management system to the dialysate flow loop, and wherein the sodium-modified fluid is generated by the sodium management system from a fluid in the reservoir for addition to the dialysate in the dialysate flow loop;
wherein the pump controls an amount of fluid pumped through the sodium management system;
wherein the conductivity or sodium ion concentration of the dialysate in the dialysate flow loop is substantially unchanged between the outlet of the dialyzer and the outlet of the bypass conduit.

2. The system of claim 1, wherein the sodium-modified fluid and the dialysate are regenerated into a physiologically-compatible dialysate with the reconstitution system, wherein only the physiologically-compatible dialysate is contacted with blood via the dialyzer.

3. The system of claim 2, wherein the physiologically-compatible dialysate comprises the sodium ion concentration measured by the conductivity detector within a predetermined range of from about 120 to about 150 mM NaCl.

4. The system of claim 2, wherein electrolytes removed from the input dialysate or input ultrafiltrate by the sodium management system are conveyed through a separate conduit and not returned or added to the dialysate in the dialysate flow loop, wherein the sodium management system is an electrodialysis system.

5. The system of claim 1, wherein the input dialysate or input ultrafiltrate is divided into first and second flow streams within the sodium management system wherein the sodium management system generates a sodium-concentrate solution from one of the first and second flow streams, wherein the sodium-concentrate solution can be passed through the dialysate regeneration unit to regenerate one or more materials or sorbents located therein by removing waste cations and replacing them with sodium in the sodium-concentrate solution;
wherein the reservoir is an ultrafiltrate reservoir, or wherein the system further comprise an ultrafiltrate reservoir for pumping the fluid into or out of the dialysate flow loop at a position downstream from the dialyzer and upstream from the dialysate regeneration unit, wherein operation of a control pump in an efflux direction causes net removal of a second fluid from blood on an extracorporeal side of a membrane in the dialyzer to generate an ultrafiltrate added to the ultrafiltrate reservoir and operation of the control pump in an influx direction causes net addition of the second fluid to the blood on the extracorporeal side of the membrane.

6. The system of claim 1, wherein the sodium management system is an electrodialysis cell comprising at least a concentrate flow channel, a diluate flow channel and an electrode rinse flow channel, wherein the sodium ions move from the diluate flow channel to the concentrate flow channel in response to an electric field wherein the sodium-modified fluid is generated in the diluate flow channel for addition to the dialysate flow loop.

7. The system of claim 6, wherein the diluate flow channel is defined by a first cation exchange membrane and a first anion exchange membrane, and wherein either:
 a) the concentrate flow channel is defined by a second cation exchange membrane; the electrode rinse flow cannel is defined by the second cation exchange membrane; and the diluate flow channel is separated from the concentrate flow channel by the first anion exchange membrane; or
 b) the concentrate flow channel is defined by a second anion exchange membrane, the electrode rinse flow channel is defined by the second anion exchange membrane; wherein the diluate flow channel is separated from the concentrate flow channel by the first cation exchange membrane.

8. The system of claim 6, further comprising an electrode rinse pump and electrode rinse reservoir for circulating the electrode rinse solution through the electrode rinse flow channel.

9. The system of claim 6, further comprising a concentrate solution and a concentrate pump for circulating the concentrate through the concentrate flow channel and an electrode rinse pump and electrode rinse reservoir for circulating the electrode rinse solution through the electrode rinse flow channel.

10. The system of claim 5, wherein ultrafiltrate directed toward the ultrafiltrate reservoir passes through the sodium management system prior to collection in the ultrafiltrate reservoir.

11. The system of claim 1, wherein the dialysate flow loop further comprises a dialysate reservoir located downstream from the dialyzer and upstream from the dialysis regeneration unit.

12. The system of claim 6, wherein the reservoir is an ultrafiltrate reservoir, or wherein the system further comprises an ultrafiltrate reservoir; and wherein ultrafiltrate passes through the concentrate flow channel prior to collection in the ultrafiltrate reservoir.

13. The system of claim 6, wherein a first flow stream passes through the concentrate flow channel prior to collection in an ultrafiltrate reservoir and a second flow stream passes through the diluent flow channel to generate the sodium-modified solution for addition to the dialysate flow loop.

14. The system of claim 5, further comprising a sodium management pump for directing the fluid from the ultrafiltrate reservoir to the sodium management system for addition to the dialysate in the dialysate flow loop.

15. The system of claim 1, wherein the sodium-modified fluid has the sodium ion conductivity or concentration determined by the conductivity detector less than the dialysate in the dialysate flow loop and thereby reduces the concentration of sodium in the dialysate flow loop upon addition to the dialysate.

16. The system of claim 1, wherein the sodium management system modifies the conductivity or sodium ion concentration by application of an electrical field.

17. The system of claim 1, wherein the sodium management system generates the sodium-modified fluid from dialysate removed from the dialysate flow loop.

18. The system of claim 17, wherein dialysate from the dialysate flow loop is directed through the sodium management system or bypasses the sodium management system using a bypass regulator having a valve that determines an amount of the sodium-modified fluid added to the dialysate.

19. The system of claim 1, wherein sodium-modified fluid from the sodium management system is added to the dialysate flow loop at a position between the outlet of the dialyzer and the single inlet of the dialysate regeneration unit.

20. The system of claim 1, wherein the sodium-modified fluid from the sodium management system is added to the dialysate flow loop through a valve at a position between an inlet of the dialyzer and the single outlet of the dialysate regeneration unit, the valve determining an amount of the sodium-modified fluid added to the dialysate.

21. The system of claim 1, wherein the sodium management system comprises a forward osmosis system having a reverse osmosis module, and a water reservoir.

22. The system of claim 1, wherein the sodium management system comprises a reverse osmosis system comprising a reverse osmosis module having a sodium rejection fraction greater than 95%.

23. The system of claim 1, wherein the sodium management system comprises at least one capacitive deionization cell.

24. The system of claim 23, wherein the at least one capacitive deionization cell can remove sodium ions by application of a voltage across two or more electrodes for generating a sodium-modified fluid having a lower concentration than the fluid entering the capacitive deionization cell.

25. The system of claim 23, wherein the at least one capacitive deionization cell can store the sodium ions by application of a voltage across two or more electrodes for generating a sodium-modified fluid having a higher concentration than the fluid entering the capacitive deionization cell.

26. The system of claim 23, wherein the at least one capacitive deionization cell comprises at least two capacitive deionization cells, wherein a first capacitive deionization cell of the at least two capacitive deionization cells can be regenerated by passing a flushing fluid through the first capacitive deionization cell while another capacitive deionization cell remains operable to generate the sodium-modified fluid by application of a voltage across two or more electrodes.

27. The system of claim 1, wherein the system is controlled compliant containing at least a dialysate pump to allow the dialysate flow through the dialysate regeneration unit and the sodium management system.

28. The system of claim 1, wherein the system selectively meters the fluid into and out of the dialysate flow loop.

29. The system of claim 1, wherein the system further comprises at least one of a control pump, a water pump, a salination pump, an acid concentrate pump, and a replacement fluid pump; and wherein the system selectively meters the fluid into and out of the dialysate flow loop using any one of the control pump, the water pump, the salination pump, the acid concentrate pump, the replacement fluid pump, and combinations thereof.

30. The system of claim 1, wherein the system provides for bi-directional flow.

31. The system of claim 1, wherein the addition of the sodium-modified fluid is controlled to a prescribed concentration or conductivity by a valve fluidly connected to the bypass conduit, wherein the valve determines an amount of the sodium-modified fluid added to the dialysate.

32. The system in claim 2, wherein increasing the conductivity or sodium concentration in the dialysate of the dialysate flow loop is not through the reconstitution system.

33. The system in claim 2, wherein the non-sodium positive ions of which the concentrations are increased through the reconstitution system include magnesium and potassium ions.

34. The system of claim 1, wherein the sodium management system generates the sodium-modified fluid from an input ultrafiltrate.

35. A method for modifying the sodium ion concentration of a dialysate for dialyzing blood using the system of claim 1, comprising:
    circulating the dialysate in the dialysate flow loop, wherein the dialysate contacts the dialyzer; wherein the at least one waste species enters the dialysate; and wherein the at least one waste species is partially removed by the dialysate regeneration unit;
    operating a control or ultrafiltration pump connected to the ultrafiltrate reservoir for pumping the fluid into or out of the dialysate flow loop at a position downstream from the dialyzer and upstream from the dialysate regeneration unit, wherein operation of the control pump in an efflux direction causes net removal of fluid from the blood on an extracorporeal side of a membrane in the dialyzer to generate an ultrafiltrate added to the ultrafiltrate reservoir and operation of the control pump in an influx direction causes net addition of fluid to the blood on the extracorporeal side of the membrane;
    modifying a sodium ion concentration of an input fluid using the sodium management system to generate the sodium-modified fluid, the input fluid being dialysate or ultrafiltrate and the input fluid divided into first and second flow streams within the sodium management system; and
    adding the sodium-modified fluid to the dialysate flow loop.

36. The method of claim 35, wherein the input fluid is a fluid removed from the dialysate flow loop at a location between the single outlet of the dialysate regeneration unit and an inlet of the dialyzer.

37. The method of claim 35, wherein the input fluid is a fluid removed from the dialysate flow loop at a location between the single inlet of the dialysate regeneration unit and the outlet of the dialyzer.

38. The method of claim 35, wherein the input fluid is an ultrafiltrate removed from the dialysate flow loop through operation of the control or the ultrafiltrate pump.

39. The method of claim 35, wherein the sodium-modified fluid is added to the dialysate flow loop at a location between the single inlet of the dialysate regeneration unit and the outlet of the dialyzer.

40. The method of claim 35, wherein the sodium management system has an electrodialysis cell with at least a concentrate flow channel, a diluate flow channel and an electrode rinse flow channel, wherein sodium ions move from the diluate flow channel to the concentrate flow channel in response to an electric field wherein the sodium-modified fluid is generated in the diluate flow channel for addition to the dialysate flow loop.

41. The method of claim 35, further comprising operating the control pump to transport ultrafiltrate through the concentrate flow channel to the ultrafiltrate reservoir.

42. The method of claim 40, wherein the first flow stream is passed through the concentrate flow channel prior to collection in the ultrafiltrate reservoir and the second flow stream is passed through the diluent flow channel to generate the sodium-modified fluid for addition to the dialysate flow loop.

43. The method of claim 35, wherein the input fluid has a pH greater than 7.0.

44. The method of claim 35, with the proviso that the input fluid is substantially free of ammonia or ammonium ions.

45. The method of claim 35, with the proviso that any addition of fluid having a sodium ion concentration higher than the dialysate in the dialysate flow loop to increase the sodium ion concentration therein is the sodium-modified fluid generated by the sodium management system using a capacitive deionization cell.

46. The method of claim 35, with the proviso that any addition of fluid having a sodium ion concentration lower than the dialysate in the dialysate flow loop to decrease the sodium ion concentration therein is the sodium-modified fluid generated by the sodium management system using a capacitive deionization cell.

47. The method of claim 35, wherein the method is controlled compliant.

48. The method of claim 35, wherein the fluid is selectively metered into and out of the dialysate flow loop.

49. The method of claim 35, wherein the fluid is selectively metered into and out of the dialysate flow loop using any one of a control pump, a water pump, a salination pump, an acid concentrate pump, a replacement fluid pump, and combinations thereof.

50. The method of claim 35, wherein bi-directional flow is provided with the dialysate flow loop.

* * * * *